US012636176B2

(12) United States Patent　　　(10) Patent No.:　US 12,636,176 B2
Johnson et al.　　　　　　　　　　(45) Date of Patent:　May 26, 2026

(54) DYNAMIC HIP ORTHOSIS DEVICE

(71) Applicant: Icarus Medical, LLC, Charlottesville, VA (US)

(72) Inventors: David T. Johnson, Charlottesville, VA (US); Evan Eckersley, Charlottesville, VA (US); Philip Miller, Charlottesville, VA (US)

(73) Assignee: Icarus Medical, LLC, Charlottesville, VA (US)

( * ) Notice: Subject to any disclaimer, the term of this patent is extended or adjusted under 35 U.S.C. 154(b) by 0 days.

(21) Appl. No.: 18/669,479

(22) Filed: May 20, 2024

(65) Prior Publication Data

US 2024/0382331 A1　　Nov. 21, 2024

Related U.S. Application Data

(60) Provisional application No. 63/467,464, filed on May 18, 2023, provisional application No. 63/468,763, filed on May 24, 2023.

(51) Int. Cl.
　　A61F 5/01　　　　　(2006.01)
(52) U.S. Cl.
　　CPC .......... A61F 5/0104 (2013.01); A61F 5/0193 (2013.01)
(58) Field of Classification Search
　　CPC ............ A61F 5/0193; A61F 2005/0183; A61F 5/0104; A61F 5/028
　　See application file for complete search history.

(56) References Cited

U.S. PATENT DOCUMENTS

| | | | | |
|---|---|---|---|---|
| 5,267,928 A | * | 12/1993 | Barile | ................ A63B 21/4025 |
| | | | | 2/70 |
| 6,652,596 B2 | * | 11/2003 | Smith | ........................ A61F 2/78 |
| | | | | 623/32 |
| 6,783,555 B2 | | 8/2004 | Kuhn et al. | |
| 7,198,610 B2 | * | 4/2007 | Ingimundarson | ..... A61F 5/0123 |
| | | | | 602/26 |
| 7,473,235 B2 | | 1/2009 | Schwenn et al. | |
| 7,758,481 B2 | | 7/2010 | Drennan | |
| 7,931,571 B2 | | 4/2011 | Bernardoni | |
| 8,172,780 B2 | * | 5/2012 | Brown | .................. A61F 5/0193 |
| | | | | 602/61 |
| 8,308,671 B2 | | 11/2012 | Nace | |
| 8,435,202 B2 | * | 5/2013 | Lartonoix | ............. A61F 5/0193 |
| | | | | 602/61 |
| 8,771,210 B2 | | 7/2014 | Smith et al. | |

(Continued)

FOREIGN PATENT DOCUMENTS

| | | |
|---|---|---|
| CN | 113116675 B | 2/2023 |
| DE | 202018002263 U1 | 5/2018 |

(Continued)

OTHER PUBLICATIONS

Application No. PCT/US2024/030287, International Search Report and Written Opinion dated Dec. 30, 2024.
Allard USA Dynamic Hip Abduction System product information as downloaded May 20, 2024; https://www.allardusa.com/products/contracture-management--rom-joints/multimotion-contracture-management/dynamic-hip-abduction-system-p38565.

(Continued)

*Primary Examiner* — Keri J Nelson
(74) *Attorney, Agent, or Firm* — Woods Rogers Vandeventer Black PLC; Nathan A. Evans

(57)　　　　ABSTRACT

A multi-axis rotational control hip orthosis that can stabilize and control forces around a hip joint and may be customized to a wearer's physical or medical needs.

29 Claims, 20 Drawing Sheets

(56)      References Cited

U.S. PATENT DOCUMENTS

| | | | |
|---|---|---|---|
| 9,393,144 | B2 | 7/2016 | Ingimundarson et al. |
| 9,468,554 | B2 | 10/2016 | Petursson et al. |
| 10,357,391 | B2 | 7/2019 | Petursson |
| 10,548,758 | B2 * | 2/2020 | Turconi ................ A61F 5/0193 |
| 10,912,666 | B2 | 2/2021 | Zistatsis et al. |
| 2003/0009120 | A1 * | 1/2003 | MacAllister ............ A61F 13/06 |
| | | | 602/61 |
| 2010/0292622 | A1 * | 11/2010 | Weissleder ............ A61F 5/0193 |
| | | | 602/23 |
| 2012/0271207 | A1 | 10/2012 | Schoen et al. |
| 2013/0184628 | A1 * | 7/2013 | Ingimundarson ..... A61F 5/0102 |
| | | | 602/26 |
| 2016/0107309 | A1 | 4/2016 | Walsh et al. |
| 2016/0193067 | A1 * | 7/2016 | Petursson ................. A61F 5/30 |
| | | | 602/16 |
| 2018/0049904 | A1 | 2/2018 | Ingimundarson et al. |
| 2020/0030179 | A1 | 1/2020 | Schwenn et al. |
| 2020/0085667 | A1 | 3/2020 | Chen et al. |
| 2024/0382331 | A1 | 11/2024 | Johnson et al. |

FOREIGN PATENT DOCUMENTS

| | | | |
|---|---|---|---|
| EP | 2720653 | B1 | 4/2014 |
| EP | 3687743 | B1 | 10/2023 |
| JP | 2023114476 | A | 8/2023 |
| KR | 102100146 | B1 | 4/2020 |
| NL | 1029086 | C2 | 11/2006 |

OTHER PUBLICATIONS

Bauerfeind Medical product information as downloaded May 20, 2024: https://bauerfeind.ca/products/coxatrain-hip-support.

Brace Orthopedic DynaCox product information as downloaded May 20, 2024; https://www.braceorthopaedic.co.uk/products/dynacox/dynacox.php.

Dall, PM, et al.; The functional use of the reciprocal hip mechanism during gait for paraplegic patients walking in the Louisiana State University reciprocating gait orthosis; Prosthetics and Orthotics International 23 (1999): 152-162, 1999; https://www.semanticscholar.org/paper/The-functional-use-of-the-reciprocal-hip-mechanism-Dall-M%C3%BCller/22a34cd699e835c0b48fbf7d30f1976d6b057701.

Enovis Excyabir Hip Brace product information as downloaded May 20, 2024; https://enovis.com/products/donjoy/excyabir-hip-brace.

Excyabir Hip Brace product information as downloaded May 20, 2024; https://www.excyabir.com/excyabir-hip-brace.

Health Products for You Aryse Tru-Range Hip Brace product information as downloaded May 20, 2024; https://www.healthproductsforyou.com/p-aryse-tru-range-hip-brace.html.

Kemker III, MD, B P, et al.; Hip and Knee Bracing: Categorization, Treatment Algorithm, and Systematic Review; Journal of the AAOS Global Research & Reviews, vol. 5 No 6 (Jun. 2021); https://www.ncbi.nlm.nih.gov/pmc/articles/PMC8189624/.

Orthoservice HIPOCROSS product information as downloaded May 20, 2024; https://orthoservice.lv/en/orthosis/lightweight-hip-brace-with-hinge-hipocross/.

* cited by examiner

FIGURE 9a                      FIGURE 9b

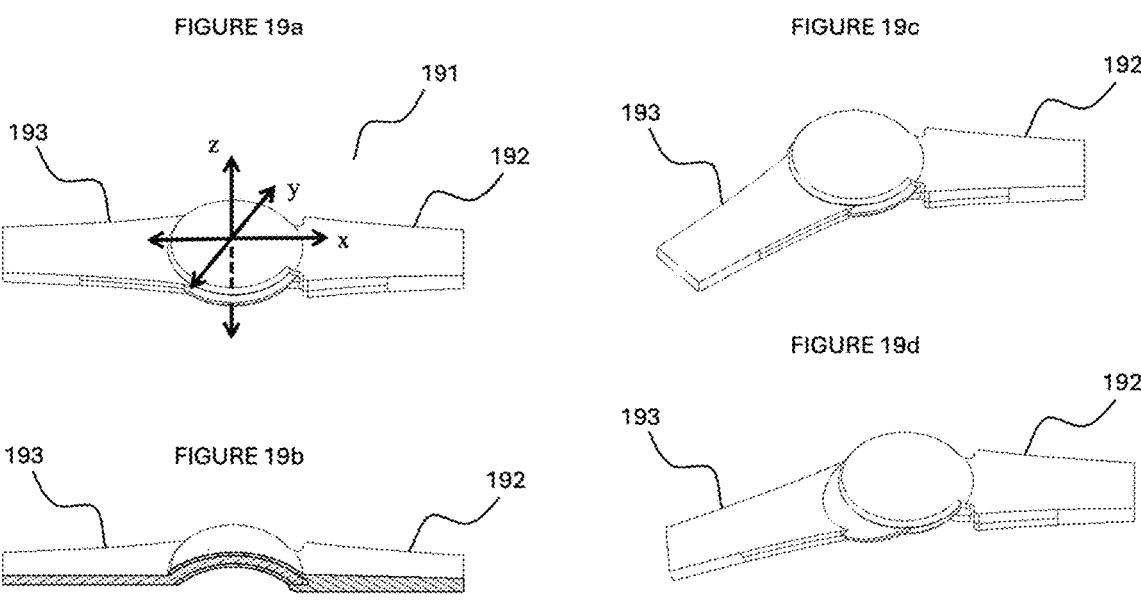
FIGURE 19a
FIGURE 19b
FIGURE 19c
FIGURE 19d
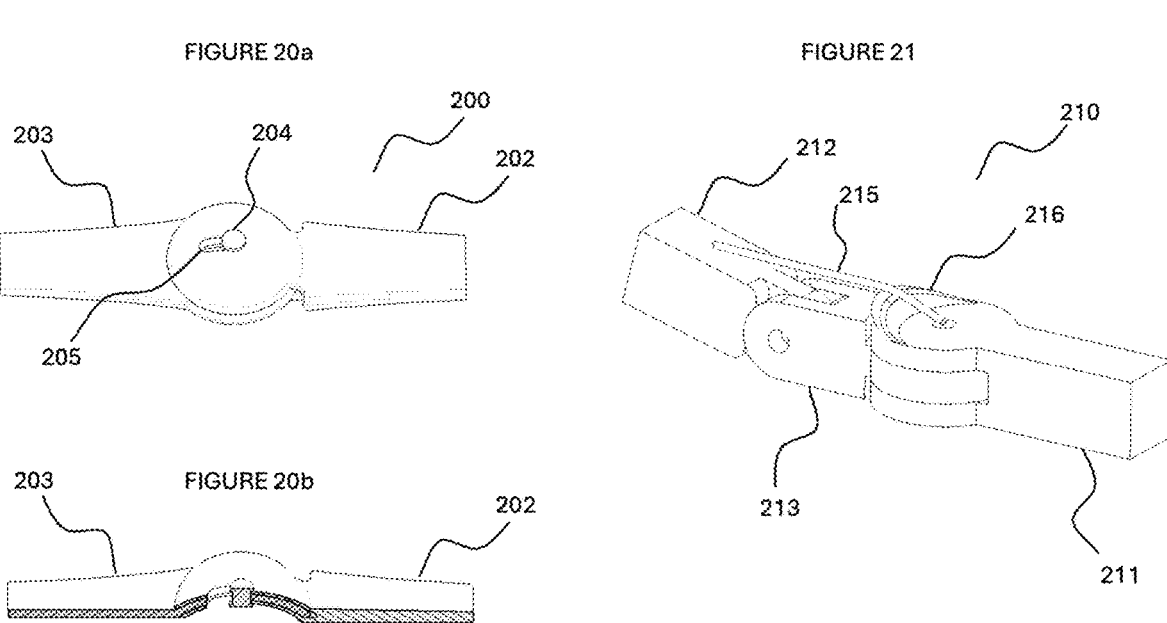
FIGURE 20a
FIGURE 20b
FIGURE 21

DYNAMIC HIP ORTHOSIS DEVICE

CROSS-REFERENCE TO RELATED APPLICATIONS

The present application relies on the disclosures of and claims priority to and the benefit of the filing dates of the following U.S. Provisional Patent Applications: U.S. Appl. No. 63/467,464, Dynamic Hip Orthosis Device, filed May 18, 2023; and U.S. Appl. No. 63/468,763, Dynamic Hip Orthosis Device, filed May 24, 2023.

The disclosures of those application are hereby incorporated by reference herein in their entireties.

BACKGROUND

Hip joint injuries and disease are a large problem in the United States. In fact, hip joint replacements are performed on just under 1% of the American population each year. Part of the reason is that the hip joint, like the shoulder joint, is a ball and socket joint with a large range of motion and bears the entire weight of the torso. In the hip joint the socket is composed of the three bones: the ilium, the pubis, and the ischium. The ball is the upper distal end of the femur. Articular cartilage covering the ball end of the femur allows the femur to glide smoothing in the hip socket. Because the hip joint bears the upper body weight it is one of the most likely joints in the body to suffer from osteoarthritis arthritis. Osteoarthritis manifests as a breakdown of the cartilage that allows the femur to glide in the hip socket. The resulting bone-on-bone contact results in significant pain and loss of range of motion.

Other hip joint problems include hip bursitis (inflammation of the of the bursa in the hip), avascular necrosis (necrosis of the distal end of the femur due to a loss of blood supply), hip dislocation (the physical dislocation of the femoral ball from the hip socket), hip dysplasia (malformation of the hip socket which results in frequent hip dislocation), among others. Many of these common hip problems are symptomatic of misaligned or insufficiently supported forces of the hip joint.

Surgery such as hip replacement is a solution for several hip joint related disorders but is expensive and comes with risks of infection and/or complications. Canes, trekking poles, walkers, and the like are non-invasive solutions that allow patients to reduce the weight borne on the hip joint alleviating some of their symptoms. Hip orthoses (bracing) may also be used to provide compression, support, or limit unwanted range of motion (ROM).

Compression braces such as the commercially available Groin Thigh Sleeve and Hip Support brace by Copper Compression™ propose to offer improved blood circulation and muscle stability. Compression braces are most often offered as a sleeve-like garment made of an elastic material. This kind of orthotic provides non-directional compression forces; that is the forces are not directed to one particular linear axis or direction but instead are circumferential or hoop stresses around the limb or body part.

Range of motion (ROM) orthotics such as the commercially available VersaROM™ Hip Brace by DJO™ are used to prevent unwanted or potentially damaging leg-hip positions such as hyperextension. These types of hip orthosis typically have an upper element that wraps around the waist and a lower element that is secured to the leg. A hinge mechanism connects the upper and lower elements and the degree of freedom at the hinge is limited by a predetermined adjustment or setting. Ideally, a ROM brace allows the joint to move unhindered within a defined range of motion. That is, a ROM brace doesn't influence, support, or assist the joint within the defined range of motion but only prevents unwanted motion.

The third type of hip orthosis provides support to the hip joint. A commercially available example of a support hip brace is the Unloader™ Hip by Ossur™. Like a ROM brace, there is typically an upper element that wraps around the waist and a lower element secured to the wearer's leg. In the case of the Unloader™ Hip, a strap is disposed diagonally between the upper and lower elements. Tightening the strap compresses specific thigh muscles which "optimizes load dispersion and proprioceptive control" of the wearer according to the Unloader™ Hip's technical literature.

Ossur™ patent publication no. 2015/0328033 describes a hip orthosis configured to reduce pain and promote mobility by means of compression of the trochanter, applying dynamic forces on the leg, and variously directed straps. The present invention differs from the article disclosed in the Ossur™ application in several ways. Just by way of example, the forces in the present invention may be adjusted "on the fly" while the orthosis is being worn by the wearer, and the forces are dynamic in that assistive forces and/or distractive forces can increase or decrease with motion. The Ossur™ application describes " . . . providing a dynamic force on the leg . . . " where the " . . . dynamic force mechanism follows the anatomical motion of the hip joint by maintaining the prescribed flexion and extension restrictions." As described in Ossur™, this is a constant force applied to the leg over a range of motion. "Dynamic" as used in this application is defined, in aspects, as a force (or forces) which varies in magnitude and/or direction in relation to the movement of the wearer's limb or joint. In addition, while the Ossur™ application describes a spring assembly to prevent adduction of the leg, the spring force is not adjustable, whereas the tension elements as described in the present invention (e.g., tensioning and compression apparatus) are adjustable. Likewise, the Ossur™ application describes semi-elastic straps that may be " . . . detachable and attachable at a plurality of predetermined locations." The purpose of the straps according to the Ossur™ application is to " . . . encourage certain movements through their elasticity and softly prevent certain movements through their resistance. The prevention of movement is neither rigid nor stops movement but rather provides feedback . . . " The tension elements and apparatus of the present invention, in aspects, primarily create forces around, between, and across the joint for specific therapeutic benefit (e.g., to change the direction or magnitude of the force vector produced by the femoral neck at the hip socket). Indeed, in embodiments of the present invention as described in this application, the forces being applied can be more than 30N, and semi-elastic straps of the kind described in the Ossur™ application would be insufficient for use in the present invention described herein.

Various attributes of the three brace types can be combined to create hybrid braces. Indeed, the Unloader™ Hip brace has aspects of a compression brace as well as a support brace; in addition to the upper waist element and lower thigh element, the Unloader™ Hip brace has integral compression shorts.

None of the three types of orthoses described above are designed to deliver dynamic force vectors across the hip joint that vary as the joint (or relevant limb(s)) is moved. None of the three types of orthoses described above are designed to be (rapidly) adjusted while the wearer is wearing the orthosis to alter the magnitude of the force for a given position or along a movement path. For example, it is well known in the literature that as the leg is moved forward, the tendency for hip dysplasia increases. The forces needed to keep the femoral ball seated in the hip socket are less when the leg is extended (in line with the torso) than when the leg is flexed. Thus, there is a need for an improved hip joint orthosis. Another example is that a person with an arthritic hip may experience pain during or in a particular position or multiple positions; a brace that can exert a precise or approximate force to reduce inter-joint contact forces near the arthritic site is needed, and not present in the prior art. This is yet another problem addressed by the current invention.

SUMMARY OF THE INVENTION

The inventions described herein comprise, in embodiments, a multi-axis rotational control hip orthosis that can stabilize and control forces around the hip joint and may be customized to the user's need. In embodiments, the present invention relates to a hip orthosis that can apply and control forces across, around, and between the hip joint, allowing the wearer to 1) reposition the bones comprising the joint, 2) apply a constant force to one or more bones of the joint, 3) apply a force that varies with the position of one of the limbs that comprise the joint, or 4) combinations thereof. Various embodiments of a hip orthosis that show how the forces across, around, and between the hip joint can be generated, positioned, varied, adjusted, and maintained are described. This orthosis can be used to relieve pain, enable certain movement while restricting others, enabling certain activities, and preventing future injuries. In aspects, this orthosis can be adjusted by the user, manufacturer, or clinician, through multiple features including 1) a tensioning or compression element, which stores energy in one or more directions across a joint 2) an adjustment mechanism for changing the amount of energy stored and resulting force within the tensioning or compression element, 3) optionally, a mechanism of changing the direction/orientation of corrective force through a series of anchors, slots, or other positioning elements and 4) optionally, a method to custom-fabricate the device to optimize the comfort and efficiency of the device's form based on the anatomy of the user.

To control the rotation and/or translation forces on the hip in one or more axes, the device may contain multiple tensioning/compression elements/apparatus to address the user's need(s). One or more tensioning/compressive apparatus may be controlled by a single adjustment of the component. These elements may be modular and can be added as needed based on the user's condition. Multiple elements can be used in this orthosis to introduce more forces in different directions to secure the hip joint. The adjustment element and mechanism can be comprised of the same components or have varying components and designs. These designs include rotary dials, levers, ratchet and pawl mechanisms, pull-straps, or tabs, and the like. In one embodiment, adjusting the component changes the direction of the forces. (For example, moving the location of an anchor point.) In another embodiment, adjusting the component changes the magnitude of the force applied. (For example, stretching an elastic element.) Combining these embodiments would allow for adjustments that change the direction of the force as well as the magnitude. The energy storage elements used in conjunction with the adjustment mechanism can be changed to affect the strength, location, and orientation of the forces.

In one embodiment, the orthosis is composed of two pieces: the thigh element portion and the body portion. The thigh element portion of the brace can be attached around the thigh of the individual while the waist portion is generally around the lower portion of the upper body and torso region. These two portions are connected through the tensioning system. This tensioning system has a series of pipes or guides connecting both portions with the tensioning cable within the pipes. These cables can have an elastic feature in series with them to create the pressure on the hip joint forces that keep the joint in place. In embodiments, the thigh portion is extendable below the thigh, and/or the body portion is extendable above the waist, if additional support and/or connection to other orthoses is desired.

In aspects, the tensioning element can be adjustable. As a non-limiting example, with the rotation of a dial, the magnitude of force can be changed. Other adjustment mechanisms, such as a slider, a toggle, a selector, or the like, could be envisioned. The larger the magnitude of the force applied, the greater the hip joint immobility within the brace, in at least one embodiment. By shifting the anchor points of the stored energy element to the brace, the direction of the forces can be changed. Anchor points on the brace can be freely moved from one point on the brace to another. The cable can be moved to existing points on the brace locked into place to change the direction of the force. The direction of force applied by the cabling system attached to the tension element can be manipulated through these moving anchor points. In aspects, the position of the anchor points may be pre-determined by a digital model of a hip joint where the positions are predicted to achieve a specific or approximate force or system of forces at one or more positions and/or throughout a range of motion.

The tensioning element in the brace can be used to supply forces onto the hip joint to ultimately prevent dislocation and minimize movement that will aggravate the region. Through a combination of anchor points and tension from the energy storage element, different force vectors can be achieved through the brace. This allows for users to change their desired force on their joints. It allows the user to pull the joint proximally, or distally, or both if needed. In this manner, the orthosis described by this invention protects the hip from further damage from dislocations.

It is envisioned that the hip orthosis could be connected to or used in conjunction with additional orthopedic or prosthetic devices using connectors (169) (see, FIG. 16), such as universal connectors. This hip brace can be connected to other braces such as a leg or back brace to further the utility of the brace in conjunction with other orthoses. Any one of these orthoses may contain a similar adjustable tensioning mechanism, which can be used individually or adjusted with a single connected adjustment mechanism.

One embodiment of this design is a more flexible hip orthosis that would be made of elastic form-fitting material. This embodiment lays sleeker and more discrete on the hip without sacrificing much of the strength and stability provided by a rigid brace. The form fitting elastic material can provide an amount of compression on the joint and keep the joint secure and stabilized. This embodiment has the advantage that it may not be noticed underneath clothing because it is, in aspects, thin and form fitting. This minimalist embodiment of the hip orthosis includes but is not limited to the tensioning element, channels or piping for the tensioning cables, the elastic materials for tension, and the form fitting orthosis that covers the upper body. Yet another additional benefit of the brace described herein is that it can more precisely assist or support the joint in at least one plane, targeting the area of the joint most needing support, so that the risk of atrophy for supporting muscles and ligaments may be reduced. Structural, conforming 3D printed parts may be integrated within soft components, and the conforming parts can be interchangeable with soft components for improved scalability of manufacturing custom parts.

The various embodiments of the present disclosure may use traditional manufacturing processes for other hip braces, and/or 3D printing to produce the components. They may also be used to fabricate positives through which negative molds are constructed for molding.

The fabrication technique allows low-cost, custom devices. It also enables manufacture of intricate parts containing internal channels and features that could not be feasibly or affordably produced with injection molding, machining, or other traditional methods of manufacturing orthotic devices, although it is envisioned that embodiments of the current invention could still be made using the aforementioned techniques. 3D printing enables efficient production of lightweight, yet durable materials. The result is an effective, lightweight, customized, and cost-effective device that can be manufactured at scale.

Using a 3D scan, components of this hip brace can be customized and fabricated for the wearer. Different portions of the brace can be rigid or flexible, with the intent to customize the fit of different parts of the upper body to create the best fit of a hip brace. Anchor points for the tensioning system can be custom fabricated from the patient's/wearer's scan. These anchor points can include locations on, but are not limited to, the thigh region, the hip region, the torso region, the back region, and the abdominal region.

The 3D scan can be used manually, automatically, or semi-automatically to fabricate a custom device through 3D printing. In aspects, algorithms, machine learning algorithms, or artificial intelligence is applied to process the 3D scan and other data in order to render a digital 3D model. In aspects, this custom fit can optimize the comfort of the brace and can maximize the effectiveness by increasing contact area on the patient, thereby evenly distributing the forces. For example, a plate that is customized from the 3D scan of the thigh will have high tension forces from the tensioning element. Having a custom fitting portion in this region will allow for these forces to be substantially evenly distributed in the area. This even distribution will be more comfortable and will apply the forces in the correct direction to secure the hip joints. It is envisioned that the device can be wholly or partially prefabricated and can be further modified by the wearer or a professional to provide the desired function. This modification can include but is not limited to thermoforming of the rigid components to improve fit, comfort, or function. Adjustments and modifications of the anchor points for the tensioning element can be used to create the correct direction of the force. 3D printing of the design allows for unique functional aspects and complex mechanical features of the brace, which would not be able to be fabricated using traditional methods. For example, in aspects, the hinge described in embodiments herein have a unique feature in that they have a "fork and spoon" coupling method. In aspects, both the leg and waist portions are continuous with their respective hinge components and interconnect easily. Adjustable extension and flexion limits can be integrated with the hinge, as well as a positional lock. A tensioning system can be added to this brace as well using such additive manufacturing methods.

In one embodiment, the tensioning mechanism and anchor points can be configured to provide a dynamic assistance wherein the forces generated by the tensioning are linked to the motion of the leg, limb, or body part. The forces may be static in some directions of motion (e.g., a hoop stress compressing the femoral ball into the hip socket over the full range of motion) but there is also a dynamic force or forces that vary in direction, magnitude, or both depending on the position of the wearer's leg, limb, or body part, in embodiments.

In one embodiment, the hip orthosis utilizes elements that are contoured to the wearer's body and produce a desired force direction by manipulating the direction and location of the anchoring points and the direction and location of the tensioning elements.

In one embodiment, the tensioning mechanism of the hip orthosis can produce a partial or directed distraction force that relieves some bone-on-bone pressure by imparting a moment of rotation on the femoral ball. This may comprise a pushing or pulling force that reduces the expected amount of force between two or more bones or contact points. Embodiments include a brace that generates a system(s) of forces that pull and/or push the hip joint apart in a desired/chosen way while wearing the brace, where the distraction force is adjustable. Such a brace can potentially reduce pain and osteoarthritis symptoms if worn overnight or on a schedule, because joint distraction has been shown to slow, stop, or reverse the progression of osteoarthritis in some patients using a different form of distraction device.

In one embodiment, the tensioning mechanism of the hip orthosis generates an unloading force that reduces the effective weight of the leg or limb to supplement the wearer's muscle force and reduce the effort needed to lift the leg or limb. This can be considered assistive and can function like an exoskeleton.

In another embodiment, combinations of the previous embodiments are presented in a single hip orthosis such that it applies a constant, substantially constant, or nearly constant force across the hip joint in a range of motion, while simultaneously providing a dynamic force in another range of motion, and/or a directed distraction force, and/or an unloading force.

BRIEF DESCRIPTION OF THE FIGURES

The accompanying drawings illustrate certain aspects of some of the embodiments of the present invention and should not be used to limit or define the invention. Together with the written description the drawings serve to explain certain principles of the invention.

FIG. 19a is an orthogonal view of a hemispherical hinge.

FIG. 19b is a sectional view of the hinge of FIG. 19a.

FIG. 19c is an orthogonal view of the hinge of FIG. 19a when rotated about the z axis.

FIG. 19d is an orthogonal view of the hinge of FIG. 19a when rotated about the x axis.

FIG. 20a is an orthogonal view of a hemispherical hinge with a pin slot.

FIG. 20b is a sectional view of the hinge of FIG. 20a.

FIG. 21 is an orthogonal view of a multi-axis hinge with a gait control mechanism.

DETAILED DESCRIPTION OF THE INVENTION

Figure 1:
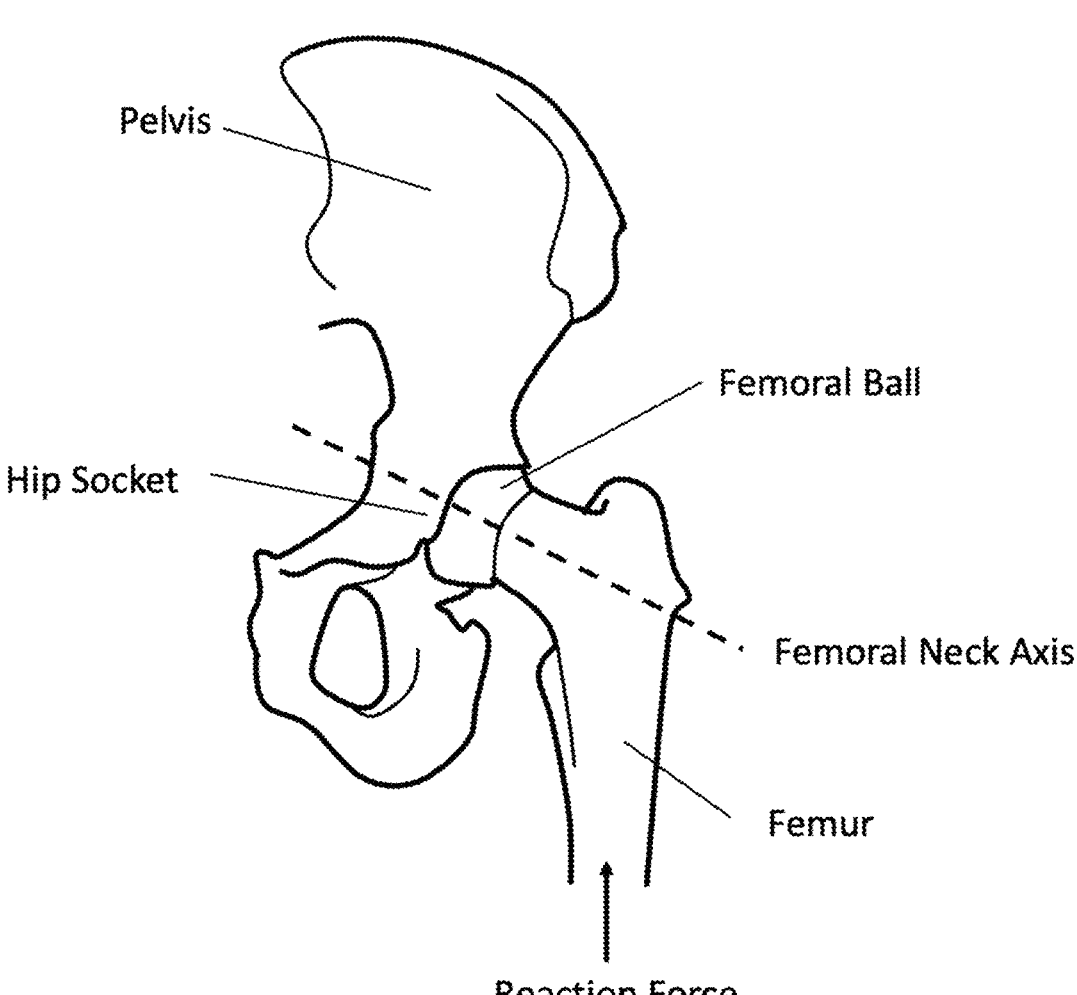
FIG. 1 is an illustration of the bones in a human hip joint.

The present invention has been described with reference to embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention. All references cited in this specification are hereby incorporated by reference in their entireties. As used herein, the term "proximal" is synonymous with top or upper, as in above the joint. The term "distal" is synonymous with bottom or lower, as in below the joint. As used herein, the term "anterior" refers to the front of the joint, body, or device while "posterior" refers to the back. Throughout the following detailed description, it should be understood that elements in tension are by example and that the same rotational force may be generated by a compression element on the opposing side of the joint. It should also be understood that the adjustable tensioning and compression apparatuses herein are described in hip orthoses by example only. One skilled in the art would recognize that similar adjustable tensioning and compression apparatuses could be applied to control rotation and forces around other joints including the wrist, shoulder, back, neck, knee, hip, and elbow. For example, the adjustable tensioning apparatus described herein could be used in an assistive knee orthosis. Throughout the following detailed description, the same reference numbers refer to the same elements in all the figures.

A dynamic hip brace is, in embodiments, an orthotic that changes the magnitude and/or direction of the force applied by the brace across the hip joint as the wearer moves their leg/hip. In one aspect of a dynamic hip brace designed specifically for post-surgical rehabilitation, it can gradually unload the weight of the leg as the wearer swings their leg forward. This enables the wearer to achieve a larger range of motion with less stress on the surgical site due to pulling of muscles and tissue. It has been shown that all manner of surgeries heal faster when the patient is able to move their body to stimulate blood flow and healing. The brace described herein can redistribute weight and pressure away from the healing hip joint to reduce stress and pain.

In addition, a dynamic hip orthosis with the adjustable tension element described herein provides controlled support and the ability to gradually increase either or both tension and range of motion as healing progresses. The adjustable tension element can include one or more ratchet and pawl dial as describe herein to change the forces across more than one axis of rotation. In aspects, the adjustable tension element can be configured to load the leg; that is, make it increasingly more difficult to extend the leg forward. This configuration can be used as a gradual extension stop—the range of motion of the leg increases as the wearer heals and becomes stronger.

A dynamic hip orthosis can also have traditional range of motion flexion and extension stops so that the absolute range of motion can be adjusted by clinicians, for example, and/or the wearer to set limits on hip movement to prevent over-extension/flexion.

A post-surgical hip brace can be optionally equipped with interchangeable components that can be added or removed to gradually increase the difficulty of post-surgery exercises. The brace may be coupled with a recovery or exercise program that may involve changing out bands or components/attachments for performing specific rehabilitative exercises directly with the brace, ensuring proper form and support during recovery.

In aspects, the post-surgical hip brace can be embedded with sensors (49) (see, FIG. 4) and connected to a smartphone app or other computer/computer program/processor. This smart brace would monitor hip joint movement, load, and alignment in real time or substantially real time. Embedded sensors (49) (see, FIG. 4) may track tension, range of motion, pressure distribution, muscle activation, and activity levels. It can provide instant feedback and alerts via a smartphone app or other computer-implemented app, helping users adjust their movements to prevent further injury, and/or accelerate recovery. The app can be configured to analyze data over time to offer personalized exercises and tips for recovery and strengthening, and allowing healthcare providers to monitor patients' progress remotely and adjust treatment plans as necessary.

While such feedback and information is particularly important for post-surgical healing regimes, such embedded sensors (49) (see, FIG. 4) may also be used for stability braces or unloading braces to give feedback to the wearer or care giver in other use applications.

The dynamic orthosis of the present invention is an improvement over traditional compression hip braces, because the amount/direction of the compressive forces (and/or tensioning forces) can be altered to provide either static or variable compression (and/or tension) support. Thus, the current invention includes an adaptable version capable of adapting to different activities and levels of exertion throughout a period of time, such as a day. The adaptive compression feature, in aspects, can automatically adjust the level of compression and/or tension based on detected activity levels, for example, ensuring optimal/ preferred/desired/chosen support during movement and relaxation. This can be used combination with other brace features as described herein.

In aspects, materials that help regulate temperature, keeping the hip joint cool during activity and warm during rest, can be integrated into the hip orthosis in the present invention. External cooling and/or heating can be coupled with, or built into, or attached to the brace. The brace can be optionally custom fit and with adjustable straps and modular components that can be tailored to fit different body shapes and sizes. A cooling system such as a NICE™ or Breg Polar™ can be attached to or integrated with the brace. Cooling/warming attachments connecting to a cooling/ warming system can be detached from the brace and/or integrated or combined with or built into the pads or other portions of the device/brace described herein.

It is envisioned that the dynamic hip orthosis of the present invention would be useful in treating many types of hip problems due the flexibility in configuring the forces across the hip joint. Such maladies include but are not limited to osteoarthritis, rheumatoid arthritis, fractures, hip labral tears, hip dysplasia, bursitis, tendinitis, avascular necrosis, snapping hip syn-drome, hip impingement, trochanteric bursitis, sciatica, hip dislocations, hip flexor strain, Perthes disease, septic arthrosis, osteonecrosis, synovitis, hip point, and stress fractures of the hip.

FIG. 1 is a schematic diagram of a typical hip joint. The femur and the pelvis meet at the ball and socket joint created by the femoral ball and the hip socket. The femur and the pelvis are joined along the axis made by the femoral neck. Ligaments and muscles (not shown) hold the hip joint together. The femoral neck axis is typically between 120 and 140 degrees as measured from the vertical. When standing upright, gravity creates a force downward, and the ground creates an equal and opposite reaction force upward as shown by the arrow in FIG. 1. Due to the angle between the reaction force vector and the femoral neck axis there is a natural tendency to push the femoral ball out of the center of the hip socket when weight is applied to the leg. In healthy adults, the concave shape of the socket along with the hip ligaments and muscles keep the hip joint properly together and well aligned.

Figure 2:
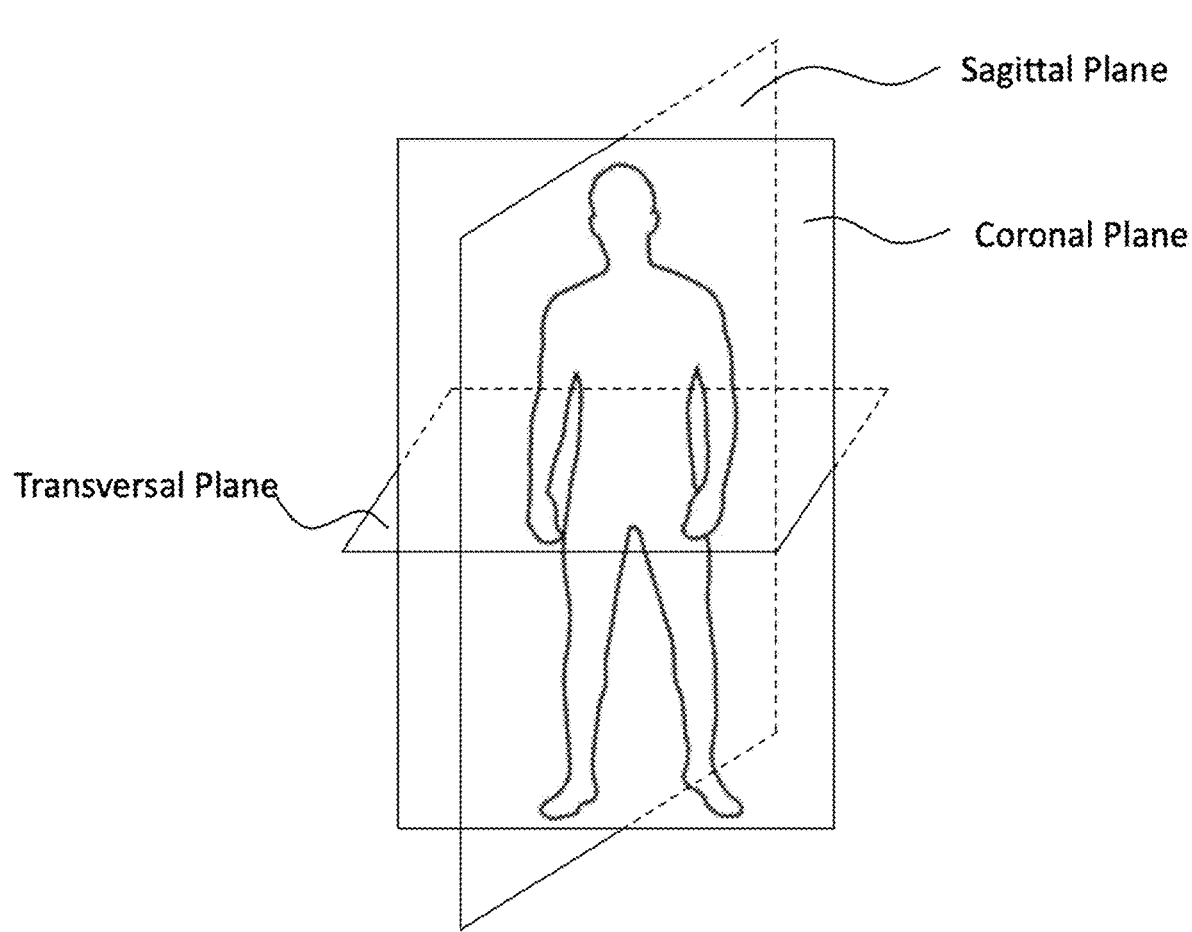
FIG. 2 is an illustration of the three orthogonal planes of the human body.

FIG. 2 is a schematic of the human body showing the sagittal, transverse, and coronal planes. Anterior movement of a leg is the forward movement within the sagittal plane. Posterior movement of a leg is the backwards movement within the sagittal plane. Abduction is the movement of a leg away from the centerline of the body in the coronal plane. Adduction is the movement of a leg towards the centerline of the body in the coronal plane. Internal rotation of the hip is the rotation along the long axis of the femur such that the toes of the foot on that leg point towards the midline of the body. External rotation of the hip is the opposite rotation such that the toes of the foot on that leg point away from the midline of the body.

Referring to FIG. 1, the femur is illustrated in a standing position. As the leg abducts from the body, it follows that the angle between the femoral neck axis and the vertical will increase, and thus, the sideways forces between the femoral ball and hip socket will also increase. Thus, both superior-anterior and inferior-anterior hip dislocations present with abduction of the leg (see, Sanders S., Tejwani N., Egol K. A., Traumatic hip dislocation—a review. Bull NYU Hosp Jt Dis. 2010; 68(2):91-96.).

Figure 3:
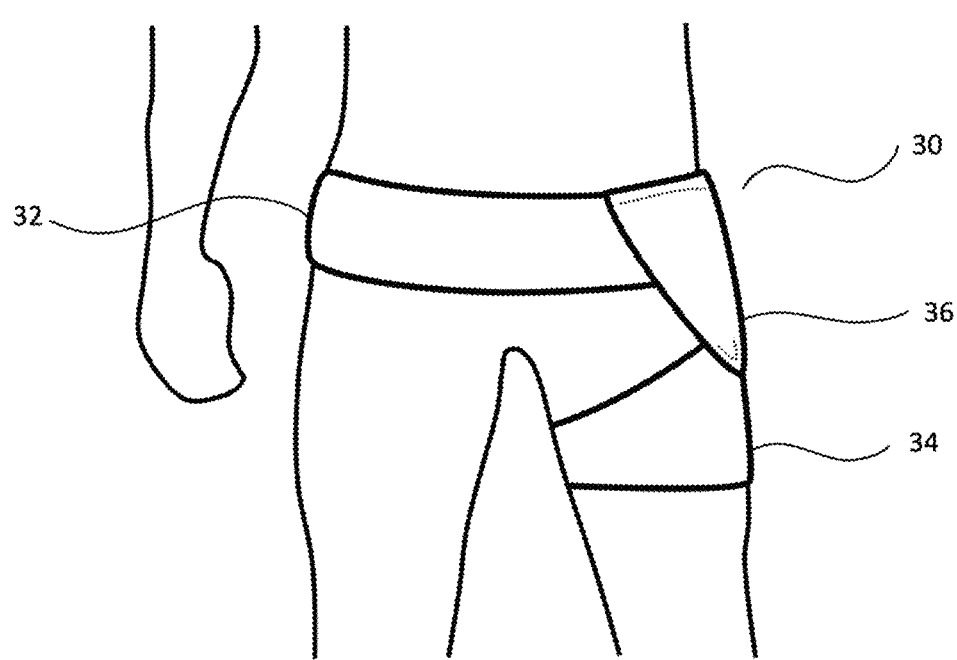
FIG. 3 shows a schematic illustration of a compression type hip brace.

Currently available compression hip braces are predominately a sleeve style garment worn over the thigh or a pant style garment worn over both thighs. This type of hip orthosis works by applying compression to the muscles of the hip and upper thigh often by means of a stretch fabric such as lycra, neoprene, and the like. FIG. 3 shows a schematic of a typical, currently-available compression hip brace (30). The predominant forces generated by compression style hip braces are circumferential around the limb (hoop stresses) via the leg cuff (34) with only minor longitudinal (along the leg axis) forces possible via the thigh patch (36) which connects the leg cuff with the waist belt (32). In addition, the magnitude of force applied is not significantly affected by the motion or position of the leg.

Traditional compression hip braces are not effective for severe hip displacement disorders. The amount of compression needed to hold the femoral ball in the hip socket is very high at large hip abductions and/or large leg flexions. Since the compression force is effectively constant from a traditional compression hip brace, the level of compression must be very high even when the leg is not abducted (e.g., lying down, standing at rest, etc.). Thus, to be effective, a traditional compression hip brace would be uncomfortable to wear for long periods of time.

While the desired direction and magnitude of the force vector across the joint may be well defined, the best combination of straps and anchor points to achieve that force vector will vary greatly from individual to individual. Strapping systems can apply a compressive force (hoop stress) where they wrap around the body part. However, the forces applied by the orthosis straps will be applied to the skin, adipose tissue, and underlying muscles, not directly to the bones of the joint. Finally, not every surface of the wearer's body is available to wear an orthosis. For example, an injury, sore, or scar tissue from a previous incident may prohibit the location of a strap/orthotic junction. For these reasons, a custom orthotic that takes into account the wearer's body shape, physiological conditions, and special requirements is needed, which is addressed by the invention(s) as described herein in the current application.

A potential problem with currently-existing compressive hip orthotics is that the compressive force is applied constantly to the wearer while the orthotic is worn. For some hip conditions, the orthotic needs to provide a large force to be effective yet the orthosis may only be needed for certain activities. For currently existing garment-type compressive hip orthoses, the orthosis is donned like a pair of shorts, and it can be inconvenient to don and doff the orthosis frequently. In addition, donning and doffing a currently-existing garment type orthosis would be indiscreet in a public setting such as an office or workplace. A currently-existing hip orthosis may be uncomfortable to wear for an extended period of time and it would not be convenient to remove the orthosis for brief periods of time when it is not needed.

For example, an orthosis to control hip dislocation needs a strong compressive force aligned along the axis of the femoral neck to hold the femur in the hip socket. Hip dislocation is more likely while the patient is bearing weight on their legs such as standing, walking, climbing stairs, etc. While sitting, the risk of hip dislocation is small. In an office setting, the compressive forces would be needed when the wearer stands to walk to a meeting but not needed once the wearer sits down. It is impractical for the user to don and doff a typical, currently-existing garment-type compressive hip orthosis for a 2 minute walk, which is a problem solved by the current invention(s), as described herein.

What is needed, and as solved by the invention(s) described herein, is a means to change the magnitude of force applied to the hip joint, the direction of force applied to the hip joint, or both as the hip is moved.

Figure 4:
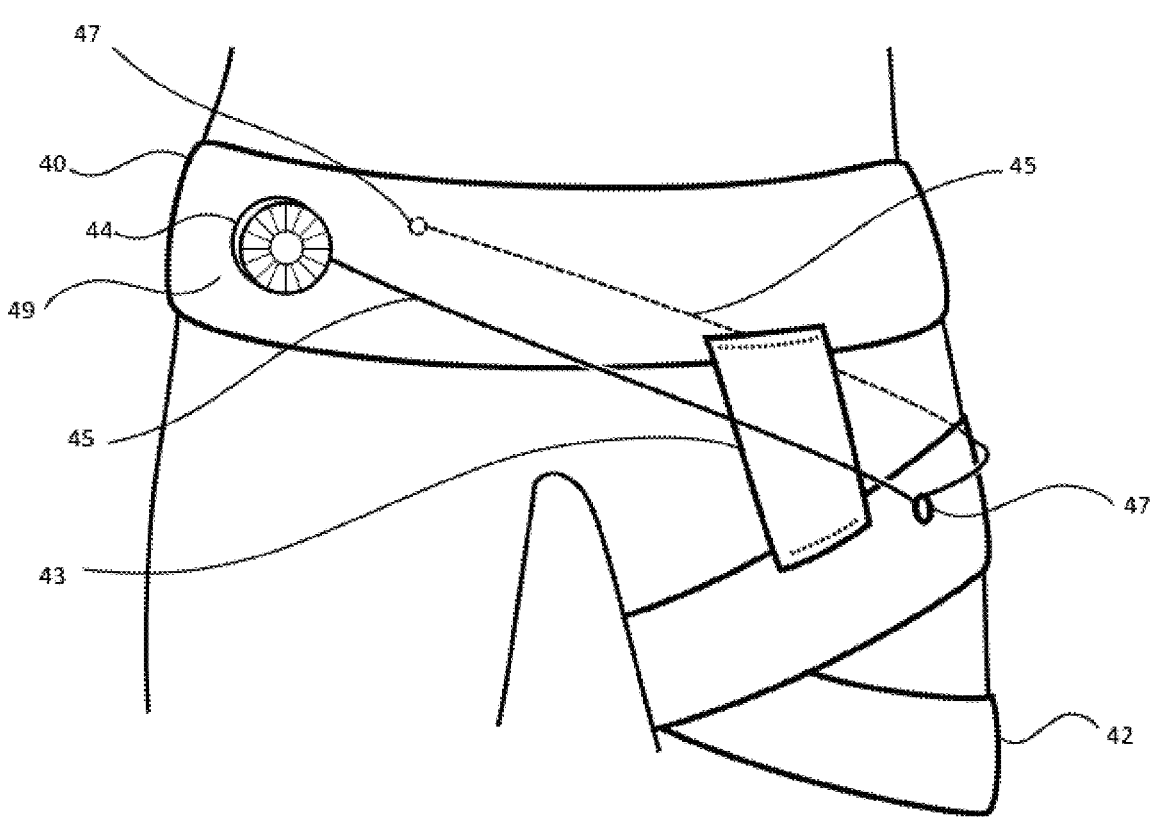
FIG. 4 shows a schematic illustration of a hip brace with a tensioning mechanism that applies a force across the hip joint.

FIG. 4 shows an embodiment of the current invention of a hip brace of the present invention. This design has at least two separate aspects to it, the thigh portion (42) and the waist portion (40). These two pieces are, in aspects, connected with a flexible tab (43) and with the tensioning element. The tensioning element can comprise a tension adjustment mechanism and a flexible cable. In aspects, an optional energy storage element may be placed in-line with the flexible cable. Attachment point(s) (47) are placed on the waist portion and at least one attachment point is placed on the thigh portion. In FIG. 4., the tension element (44) with its cabling system (45) is the primary means of aligning the position of the thigh portion with the position of the waist portion. In aspects, the flexible tab (43) is replaced with a more substantial connection that provides the primary means of aligning the positions of the thigh portion and waist portion; the tension element can be used to adjust the relative positions of the thigh portion with respect to the waist portion. The cabling system (45) of the tensioning element (44) as shown in FIG. 4 may be made from substantially flexible, yet inextensible materials such as wire cable, braided cord, string, lace, chain, rope, straps, banding, ribbon, and the like. Alternatively, the tensioning element can incorporate or be connected to elastic material/device such as a spring, pneumatics, rubber, thermoplastic polyurethane, and the like.

The thigh portion design of this embodiment of the hip brace is secured around the leg of the user, for example, with a strapping system. The thigh portion can also have different anchor points to which the tension element can be anchored. The attachment points can be made of an elastic or inelastic material; if made from an elastic material the anchor points can serve as or aid with the energy storage element of the tension element. In aspects, the thigh portion can also attach to the waist portion through optional straps, tabs, fabric, connections, and the like, to add more strength to the system.

Figure 5:
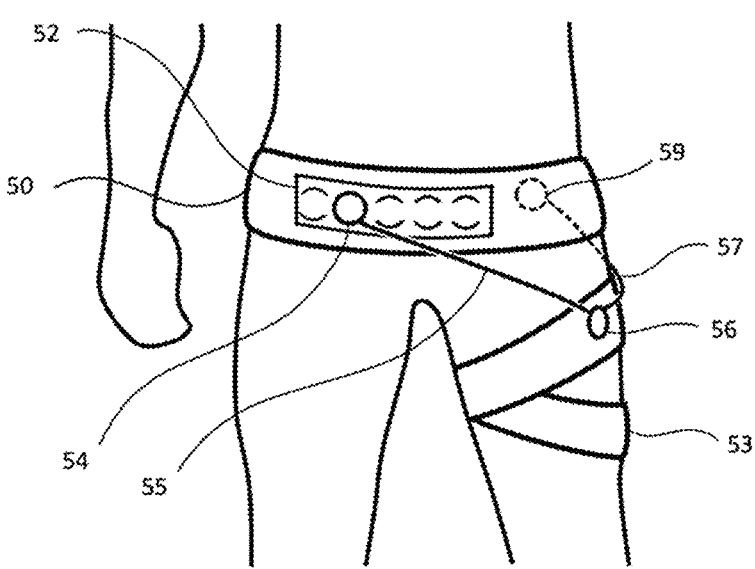
FIG. 5 shows a schematic illustration of a hip brace with an adjustable attachment mechanism for the tensioning element.

FIG. 5 shows an alternative embodiment. In this example the anchor or attachment points are not permanently fixed but may be positioned or repositioned as needed. An anchor holder (52) is mounted to the waist portion (50). An adjustable tensioning element (54) is fixed in the anchor holder. A flexible cable (55) connects the adjustable tensioning element (54) to at least one anchor (56) positioned on the thigh portion (53). A second flexible cable (57) connects the thigh portion anchor (56) to a second anchor (59) mounted on the waist portion. In aspects, the first flexible cable (55) and the second flexible cable (57) may be a single unitary cable and the anchor (56) is configured to allow the flexible cable to slide through it. By selecting a different position in the anchor holder (52) the direction of the force vector created by the tensioning element can be changed. In this manner, the hip orthotic can be customized to a specific wearer or altered as the wearer's needs change.

The anchor holder (52) shown in FIG. 5 is not intended to be limiting. Instead of a linear array of discrete anchor positions a two-dimensional array, a pattern (e.g., a hex pattern), or random distribution of discrete anchor positions are all potential possibilities. Alternatively, a continuous disposition of anchor points can be beneficial (for example, if the anchor points had Velcro™ hooks on the back and the upper element was covered partially or entirely with Velcro™ loop). Preferably, the anchoring mechanism is strong enough to withstand the forces applied by the tensioning element.

FIG. 5 shows an anchor holder for one of the upper element anchors. In an alternative embodiment, adjustable anchor holders are provided for some or all of the anchors in the present invention. Likewise, there may be more than one anchor that needs to be configured on the lower element to achieve the correct force vector to correct the hip joint dysfunction.

The waist portion, thigh portion, or portions thereof can be customized to the user by adapting their shapes from 3D scans of the waist and/or leg. The resulting designs can be 3D printed from rigid or semi-rigid materials which are preferred because they are better able distribute the forces from the tensioning element.

The tensioning elements in FIGS. 4 and 5 are used to apply force or forces across the hip joint. The tensioning adjustment mechanism can be removably or permanently attached to the hip brace. If the tensioning adjustment mechanism is removable, a means for fixing the applied tension to the flexible cable can be provided so that the hip brace can function properly when the tensioning adjustment mechanism is removed.

Figure 6:
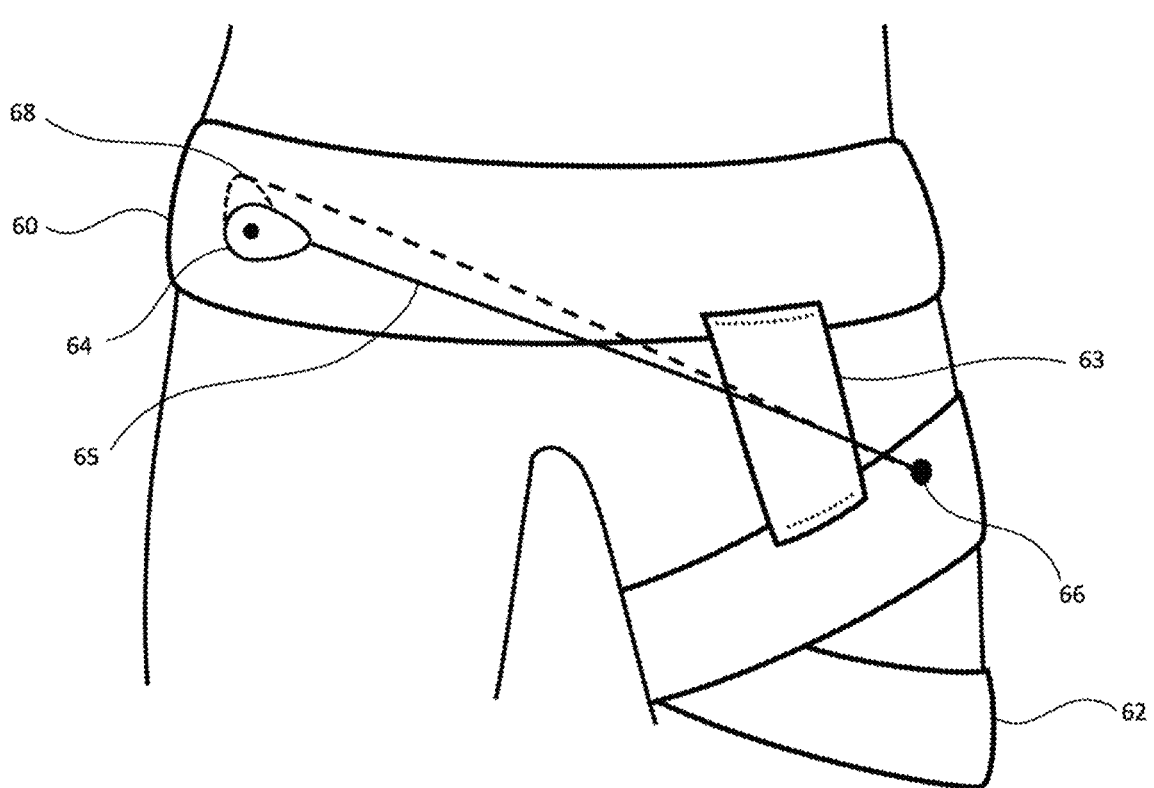
FIG. 6 shows a schematic illustration of a hip brace with a cam/lever mechanism to engage and disengage the tension force across the hip joint.

FIG. 6 shows another aspect of the hip brace. A waist portion (60) and a thigh portion (62) are connected by a flexible tab (63). A rotatable cam or lever (64) is attached to the waist portion. One end of a flexible cable (65) is attached to the cam and the second end of the flexible cable is connected to an anchor or attachment point (66). As shown, the rotatable cam is in the disengaged position wherein the force applied by the tension cable is the smallest. A second position (68)—as shown by the dashed lines—is the engaged position at which the flexible cable is applying the maximum force between the waist portion and the thigh portion. If configured with the two positions indicated, the cam would fully engage or disengage the tensioning means. In other embodiments, multiple stops could be employed so that the amount of tension between the waist and thigh portions could be increased by increments.

Figure 7:
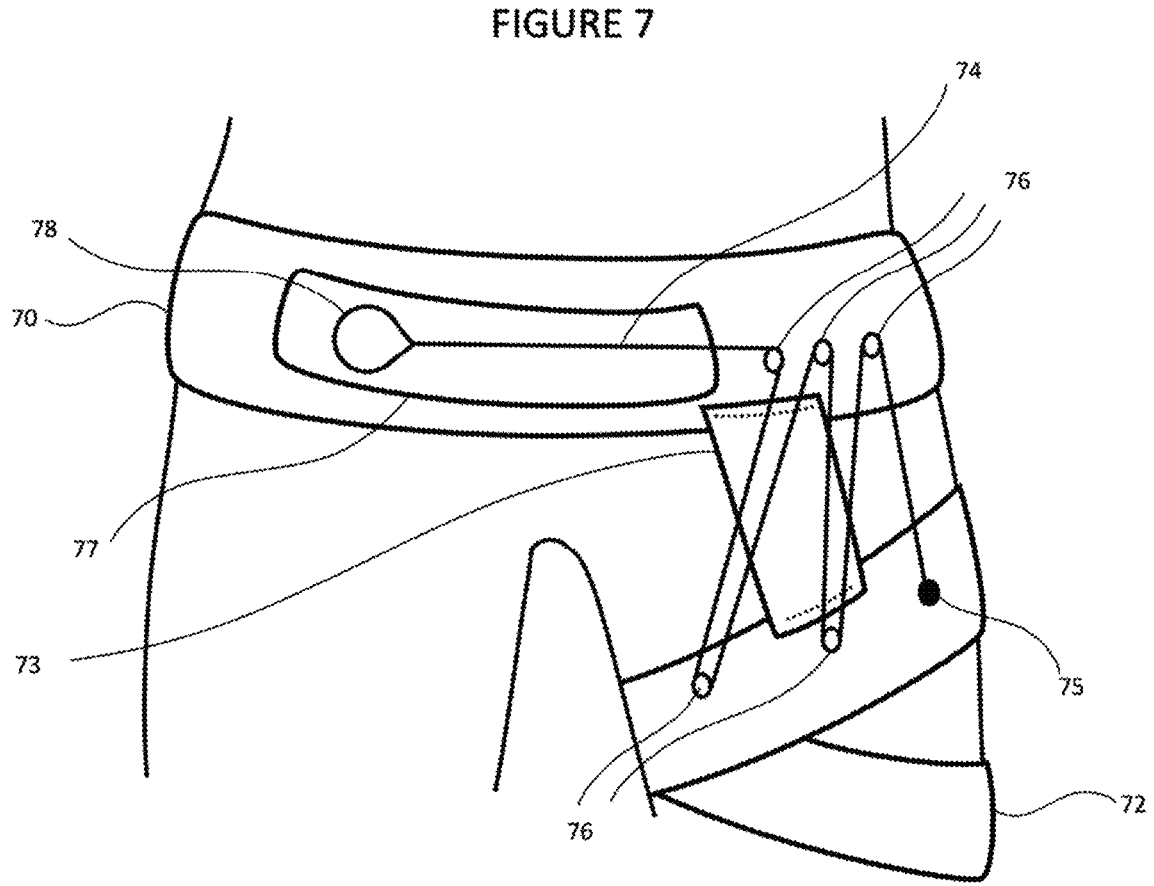
FIG. 7 shows a schematic illustration of a hip brace with a mechanism to increase the force applied across the hip joint compared to the force applied to the tensioning tab.

FIG. 7 shows another embodiment of the hip brace. A waist portion (70) and a thigh portion (72) are connected by a flexible tab (73). A first end of a flexible cable (74) is fixed to an anchor or attachment point (75) on the thigh portion. The flexible cable transverses a series of guides, pulleys, or loops (76) affixed to the waist portion and the thigh portion. The second end of the cable is fixed on a tab (78) with a Velcro-type hook on one side. A patch (77) of Velcro-type loop is attached to the waist portion. The amount of tension applied across the hip joint is determined by the location of the placement of the tab (78) on the patch (77). The multiple guides, pulleys, or loops (76) magnify the force applied across the waist portion and thigh portion versus the force applied to the tab like a block and tackle mechanism.

Figure 8:
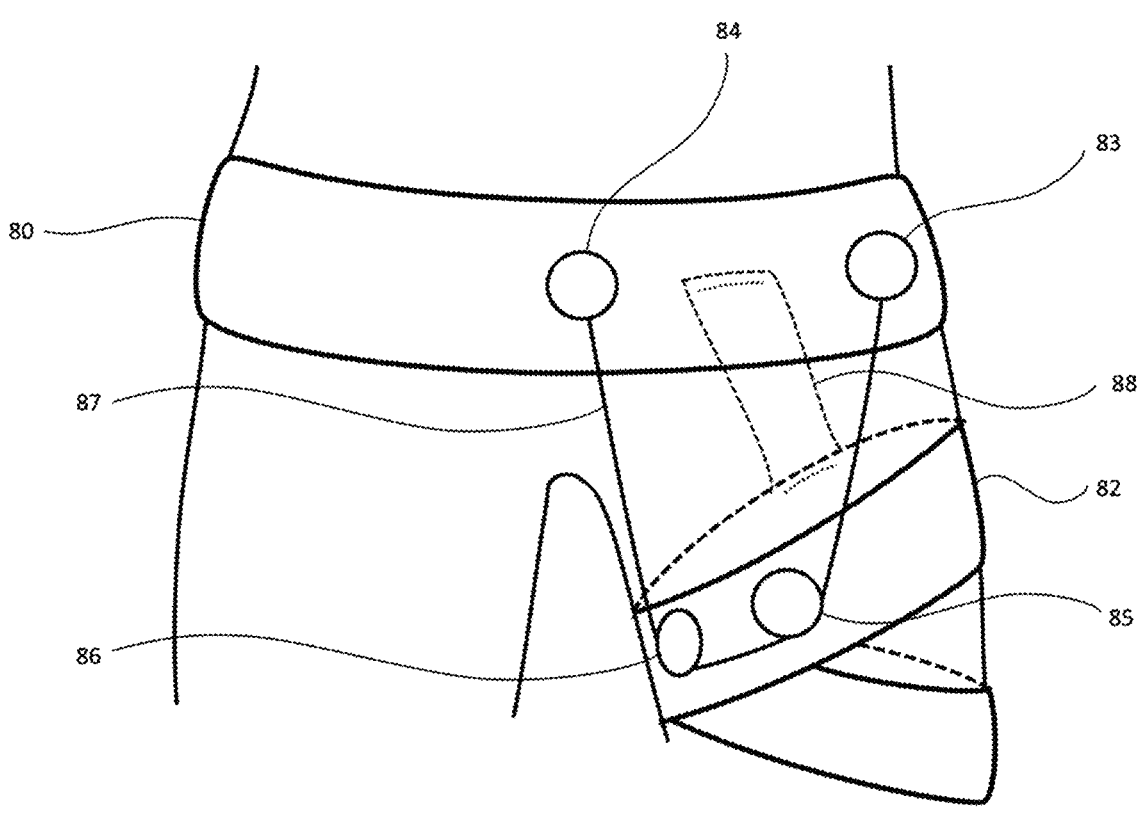
FIG. 8 shows a schematic illustration of a dynamic hip brace wherein the magnitude and direction of the force vector across the hip joint varies with the position of the wearer's leg.

FIG. 8 shows another embodiment of the present invention. An elastic web (88) is anchored (e.g., sewn) to the posterior of the waist portion (80) and the posterior of the thigh portion (82). A tensioning element (87) runs from a first anchor point on waist portion (83), to two guides on the thigh portion (85, 86), and to a second anchor point (84) on the waist portion. A tensioning adjustment mechanism is preferably attached at the outward anchor point (83). The anchor points on the waist portion are shown in an anterior position. One guide (85) on the thigh portion is predominantly in an anterior position and the other guide (86) is predominantly in a medical position of the thigh portion.

As configured, the tensioning force between the waist portion and the thigh portion due to the elastic web (88) predominantly in the sagittal plane, increases as the wearer moves their leg anteriorly and decreases as the wearer moves their leg posteriorly. The tension due to tensioning element (88) is effectively constant regardless of motion of the leg in the coronal plane or due to rotation.

There is an additional tensioning force between the waist portion and the leg cuff due to the tensioning element (87). Because of the location of the guides on the thigh portion (85, 86) lie approximately in the sagittal plane, motion of the wearer's leg in the sagittal plane does not change the force on the tensioning element (87) substantially. However, abduction of the leg in the coronal plane increases the force applied by the tensioning element (87). Likewise, external rotation of the wearer's leg increases the force on the tensioning element (87). The forces applied across the hip joint are the sum of the vector forces due to the elastic web (88) and tension element (87). The magnitude and direction of the sum of the forces across the hip joint is dynamic and changes as the leg is moved in the sagittal and coronal planes and/or rotated.

In embodiments, the tension adjustment element/mechanism for the tensioning element is attached on the waist portion of the brace. One end of the flexible cable is connected to the tension adjustment element/mechanism such as a rotary dial. An elastic material is preferably placed in line with the flexible cable and the other end of the flexible cable is connected to the thigh portion. Alternatively, the elastic material is connected to the thigh portion and the flexible cable is connected to the elastic material. In the latter case, the elastic material is secured into the thigh portion anchor points. The flexible cable can pass through a series of channels or guides in the hip brace so that it is not exposed. In one aspect, a thigh portion anchor is located on the front of the thigh. The tensioning element would have the effect of pulling the leg forward. This limits the mobility of the hip backwards. In addition, the cable system can be run around the back to the leg to pull the joint backwards and limit the mobility of the hip with its forward movement.

Figure 16:
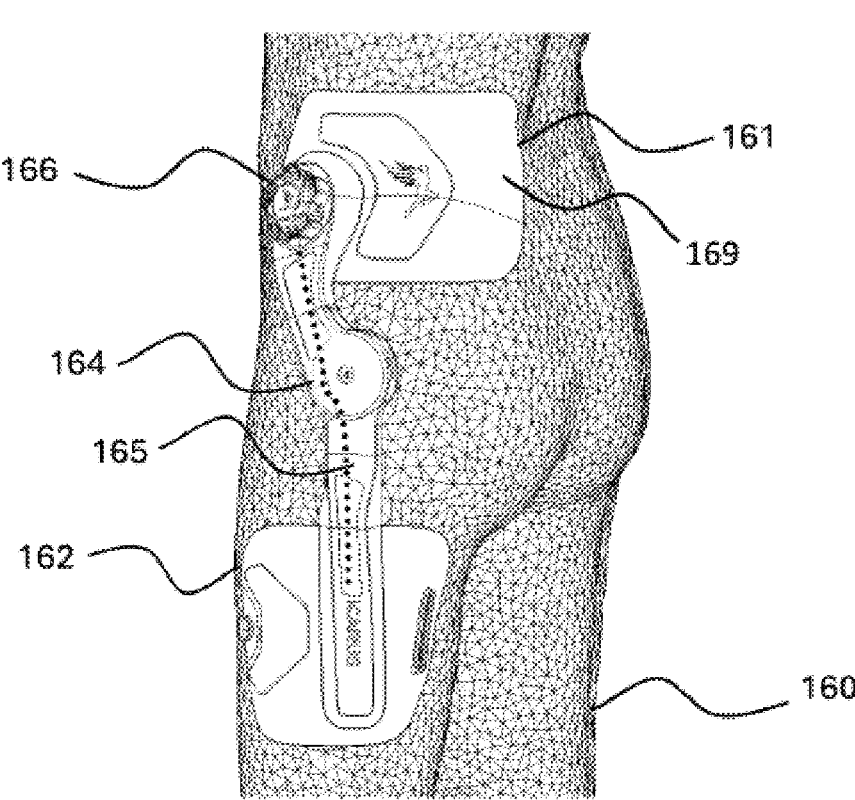
FIG. 16 shows an orthogonal view of a post hip surgery hip orthotic.

FIG. 16 shows an orthogonal view of a 3D printed hip brace suitable for some post-surgery applications. A 3D scan of the patient's waist and thigh is converted to a digital .stl file (160) and imported into a CAD program. A waist portion (161) is modeled to fit the contours of the waist section of the patient's waist. The location and size of the waist portion is optimized to avoid the surgery incision site while providing secure connection and support to the patient's body. Similarly, the thigh portion (162) is modeled to fit the contours of the thigh section of the patient's body. The thigh portion and the waist portion are connected via rigid or semi-rigid arms that meet at a hinge (164). As depicted in FIG. 16, the axis of rotation is aligned with the patient's femoral neck axis so that the hip orthotic mimics the natural rotation of the hip in the sagittal plane. The hip orthotic of FIG. 16 prevents unwanted hip abduction in the coronal plane and rotation in the transversal plane. The path of a tension element (not shown) is shown by the dotted line (165). Increasing the force on the tension element by means of the dial (166) creates a rotational force that lifts the patient's thigh (and leg). In this manner, the effective weight of the leg is reduced allowing the patient to lift the leg affected by their surgery with less muscle effort and stress on the surgical site.

The hinge as depicted in FIG. 16 is disc shaped and has a single axis of rotation which can be appropriate for some post-surgical orthotics. In other aspects, the hinge could be a section of a hemisphere which would allow the waist portion and thigh portion to rotate/translate in more than one axis to better mimic the natural motion of hip joint—which is composed of the femoral ball and the hip socket as shown in FIG. 1.

FIG. 19a is an orthogonal view of a hemispherical hinge (191). One arm of the hinge (193) is cupped between the two sides of the arm (192) as shown in the sectional view shown in FIG. 19b. Rotations of the arm (193) around the x, y, and z axes in any combination are possible when the arm (192) is held fixed. FIG. 19c shows rotation of one arm (193) around the z axis. FIG. 19d shows rotation of one arm (193) around the y axis.

A hemispherical hinge would allow freedom of movement which is appropriate for an orthotic whose purpose is to augment the wearer's natural movement and not limit it, by way of example. Depending on the purpose of the hip orthotic, a single axis hinge, two orthogonal single axis hinges, a partial multi-axis hinge, combinations thereof, or a full multi-axis hinge, can be selected as appropriate for the need of the patient/wearer. In aspects, the 'hinge' may be virtual. For example, a piece of cloth, leather, a garment, or other flexible material may serve to direct the forces of the tension element and guide the motion of the joint without a traditional hinge. The ability to manipulate forces across the hip joint can be accomplished with any of the hinges described above by selecting the path/position of the tension element and where it connects to the orthotic. A hinge, as used herein, is the area where two portions of the device are connected and rotate and/or move with respect to each other, and as would be understood by one of ordinary skill in the art.

The path of the tension element (165) in FIG. 16 passes to the anterior of the axis of rotation of the hinge (164). Lifting the leg causes the path length to decrease. Applying a force to the tension element creates a torque which aides in lifting of the leg. If the path were positioned posterior to the axis of rotation of the hinge, the tension element would provide a counter-rotational torque that would aid in drawing the leg backwards out of flexion. The tension element may optionally include an elastic energy storage element.

The path shown in FIG. 16 is generally circular around the hinge (164). A path with a uniform radius generates a linear force with respect to flexion angle. Alternatively, the path may have a radius that varies with the flexion angle of the thigh portion such as would be generated with internal cams, stops, or the like. Using a variable radiused path allows for the force to be non-linear with respect to the flexion angle. Depending on the path of the tension element around the hinge, the force may be configured such that it increases non-linearly, plateaus beyond a flexion limit, or only occurs between specific angles of flexion.

Figure 17:
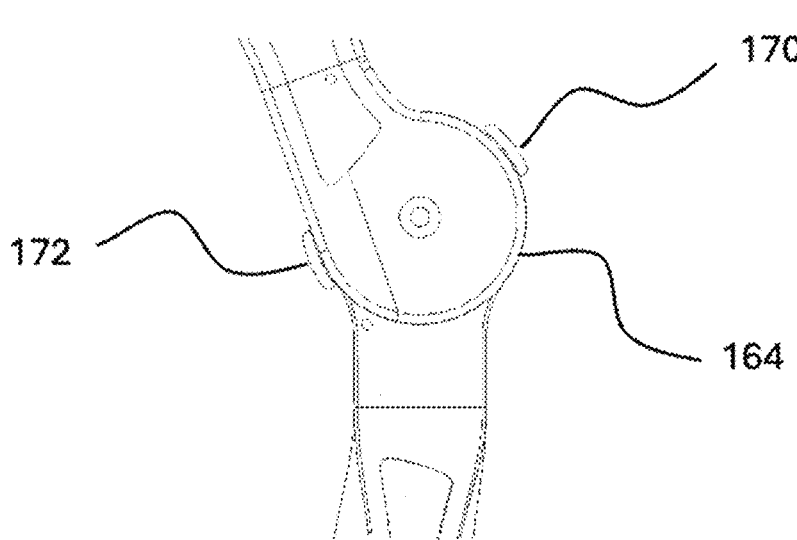
FIG. 17 is an enlargement of the hinge component of FIG. 16.

An enlargement of the hinge (164) is shown in FIG. 17. In embodiments, a flexion stop (170) and an extension stop (172) are used to limit the range of motion of the hip orthotic to prevent over-flexion and/or hyper extension of the leg during recovery.

In another aspect, the path of motion of the leg may be altered or guided by a combination of the forces applied by the tensioning element(s) and/or the degrees of freedom of the hinge(s).

Figure 18:
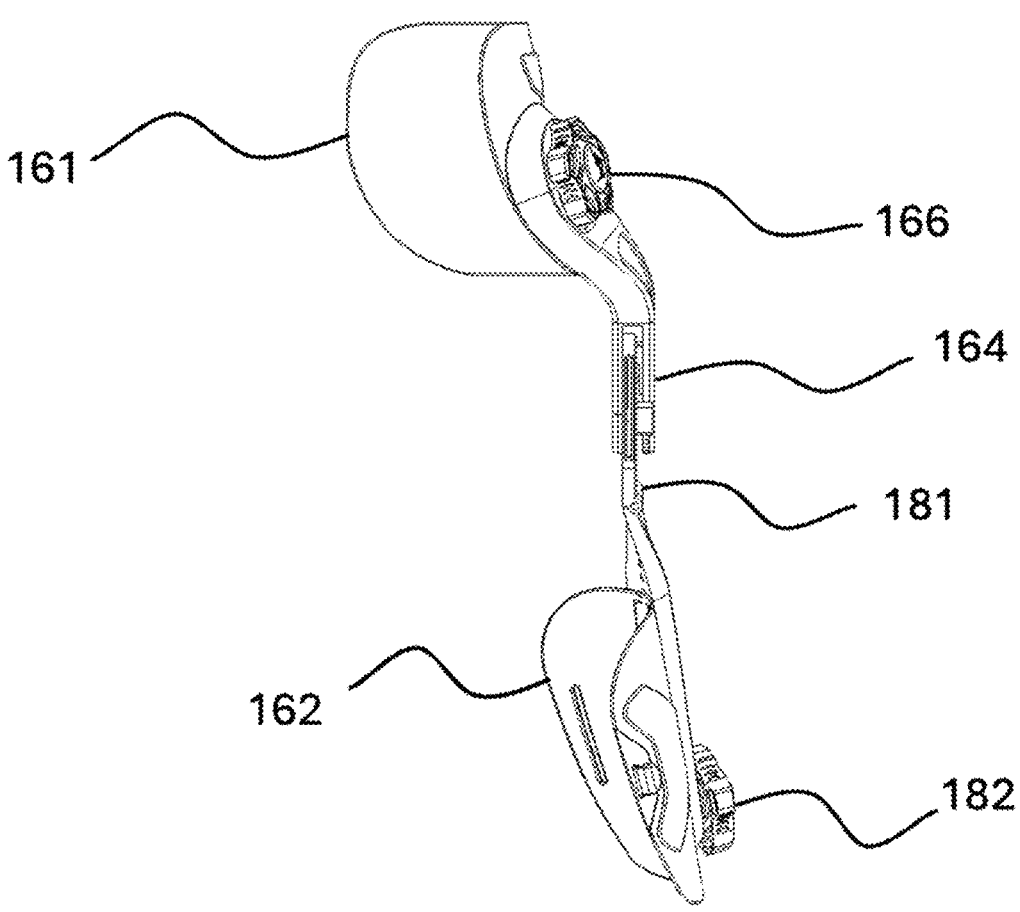
FIG. 18 is a front view of a hip orthotic with two independent energy storage elements to apply forces along two different axes of the hip joint.

FIG. 18 is another aspect of the hip orthotic described herein. In addition to the waist portion (161), thigh portion (162), hinge (164), and dial (166), as described above, there is an additional hinge (181) on the arm that connects the thigh portion to the hinge. This hinge has a single axis of rotation perpendicular to the coronal plane and allows the leg to swing in the coronal plane (abduction) and would be helpful for patients with gluteal abduction deficiency. This hinge may optionally be configured with stops to limit the range of motion in the coronal plane. The path of the tension element as depicted in FIG. 16 could end prior to the hinge (181) or continue past the hinge. In this latter case, applying a force to the tension element would pull the leg forward in the sagittal plane while simultaneously pulling the leg away from the body in the coronal plane. Alternatively, as shown in FIG. 18, a second dial (182) with its own tension element (not shown) could independently apply a force to assist abduction. The hip orthotic shown in FIG. 18 can adjust the lifting force of the leg in the sagittal plane and the swing assist force of the hip in the coronal plane thereby providing two independent forces across the hip joint. In aspects, an elastic energy storage element is connected to the tension element.

In aspects, the waist portion of the brace has straps to fit the brace to the torso area. These straps can be tightened or loosened depending on the fit of the brace on the wearer. In addition, elements can be attached to this waist area like the thigh portion area. In this embodiment, they are illustrated like panels or plates. These portion of the device can be used to change the anchor points of the cabling system as well as spread out the forces on the waist area due to the tension in the cable system. These portions can be made using a 3D scan of different torso areas and printed using a 3D printer. These portions can conform to the wearer by employing the scanned torso areas to custom fabricate the units. This can increase the surface area in contact with the wearer, spreading the forces more evenly through the portion or different portions. These portions can be, but are not limited to, attached to the abdominal region, the inside thigh region, on top of the hip, on the lower hip, and on the lower back.

With the tensioning element pulling on either side, the hip joint is restricted. If the mechanism is attached to the front of the thigh portion, the leg is then pulled forward. This ultimately limits the leg's ability to move backward. This is the opposite for hip braces used to apply a force to pull the leg backwards. When the tension on the thigh portion is pulling the wearer's leg backwards, due to the thigh portion being attached from the back of the leg, it limits the ability of the hip joint to allow the leg to move forward. In either case, both of these hip orthotics are pulling the femoral head up and into the hip socket. This secures the hip joint in place by limiting the motion of the femoral head downwards.

FIG. 8 is an illustration of a dynamic hip brace with a tensioning element that applies an approximately constant force to a hip joint when it is moved predominantly in the sagittal plane and applies a variable force to the hip joint when it is moved predominately in the coronal plane.
Form Fitting Brace Another embodiment a brace according to the present invention is a form fitting hip brace with a tensioning element. This design can be worn under clothes while also maintaining strength and security in the joint. This form fitting brace also provides compression on the joint. In this embodiment, the thigh portion and waist region are all one piece. The brace fits like a piece of clothing. With the leg in the thigh portion region and the user's waist inside the torso part of the brace, it is securing the joint in place.

A form fitting brace may not provide as much joint motion control as embodiments that use rigid and semi-rigid elements, but the tensioning system described herein is still applicable. The channels for the flexible cables can be incorporated into the form fitting brace or can be positioned on the outer surface of the brace. There can be an elastic element attached to the thigh portion of this brace. Applying pressure around the hip joint (e.g., a hoop stress) helps keeps the hip joint in place.

Figure 9:
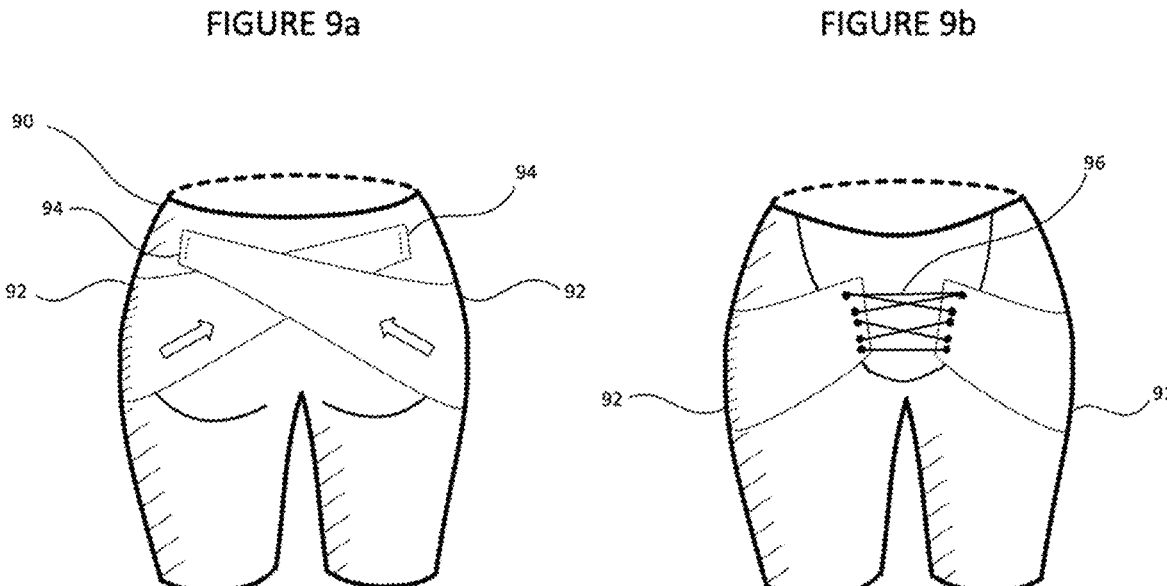
FIGS. 9a and 9b show an illustration of a hip orthosis suitable for controlling hip dislocation.

FIGS. 9a and 9b show an embodiment of a hip orthosis suitable for controlling hip dislocation. FIG. 9a is the posterior view of a garment (90). The garment could be made from cotton, polyester, lycra, or any of the natural or synthetic fibers or blends common to the fabrication of garments. In aspects, attached to the garment are two wings (92). The wings contour the body of the wearer and apply a force to the hip joint. The wings could be made from the same fabric choices as described above, netting, or fabric that has been reinforced to prevent it from stretching excessively. The wings can be attached to the garment in the back by tabs (94). The location of the tabs and the position of the wings at the hips directs the forces applied to the hips in the directions shown by the block arrows in FIG. 9a. Preferably the wings are shaped to cup the hips by using a 3D scan of the wearer's torso and legs to transfer the wearer's dimensions to the wing design. Shaping the wings to match the wearer's body aids in controlling the migration of the wings away from their ideal position. FIG. 9b is an anterior view of the garment (90). The wings (92) wrap around the hips to the front of the wearer. A tightening system (96) (here shown as a crossed lace system) allows the wearer to apply the force needed to hold the femur in the hip socket. Releasing the tension on the tightening system can be accomplished by loosening the laces without removing the entire compressive hip orthosis garment.

Figure 10:
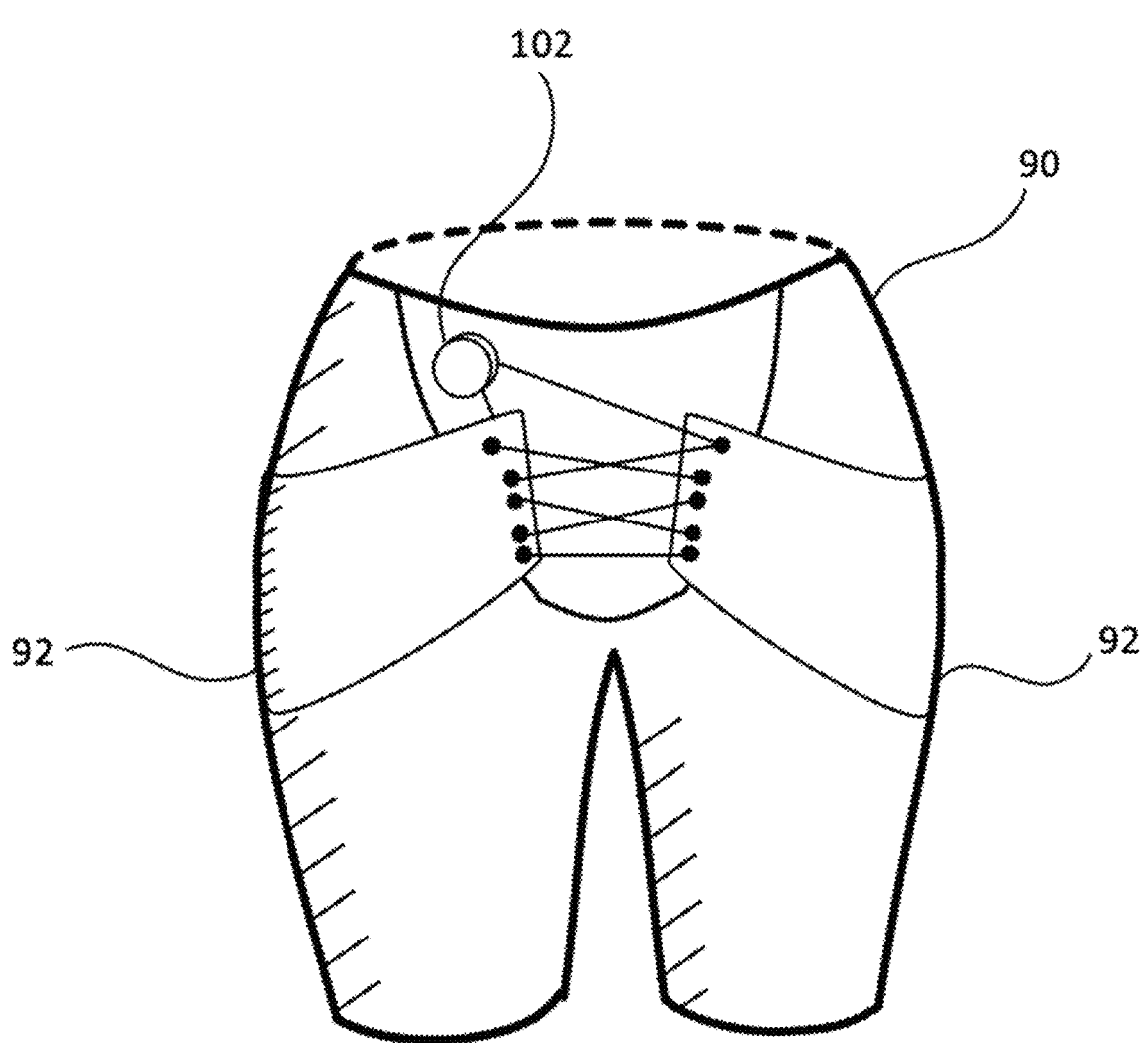
FIG. 10 shows an illustration of the hip orthosis of FIG. 9b with a ratchet and pawl dial.

FIG. 10 shows an anterior view of alternative embodiment. A ratchet and pawl (102) dial is used instead of the crossed lace system. Turning the dial tightens flexible cables secured to the distal ends of the wings (92) at the front of the garment. For convenience and comfort, the dial is positioned off center of the garment, in aspects. Unlike the crossed lace system, the dial can be operated by one hand. In aspects, release of the dial is accomplished by a push button, and the tightening and release of the forces applied by the wings is, in examples, more discreet or easy for the wearer than tying and loosening crossed laces.

Similarly, a lever or cam could be employed by itself or in conjunction with another tightening means to tighten and loosen the tension to the wings.

An adjustable tensioning element allows the user to adjust the amount of immobilization of the joint. Twisting the dial can increase or decrease the amount of tension in the system, ultimately changing the forces on the leg joint. The tensioning element pulls the leg joint in the chosen direction to limit the mobility and keep the joint in place. These forces are, at least in part, what keep the leg from further damaging itself due to dislocations.

The garments shown in FIGS. 9a, 9b, and 10 can be like shorts. Alternatively, the wings (92) can be flexibly attached to the garment. The attachment can be a sliding means (such as a line through a loop) or a loose means (such as by a length of thread). Attaching the wings in such a manner keeps the wings in place in the coronal plane (up and down)

but allows them to move around the transverse plane (around the hips front and back). The combination of contouring the hip and the flexible attachment method is able to keep the wings in the optimum position to apply a force that effectively holds the femur in the hip socket.

Alternatively, the shorts could be replaced with a waist belt since the attachment points of the wings (94) are along the waist of the wearer. In aspects, a waist belt could be easier to don and doff, easier to conceal under traditional clothing, and could be cooler to wear.

The wings could be wholly or partially made from a semi-flexible material such as a nylon, polyolefins, plastics, composites, and the like, that have been shaped to match the contour of the wearer's body. The semi-flexible nature of the wings would help hold them in the proper position, but they may be uncomfortable to sit upon. Foam padding or the like could be used to make contact with the wearer's body more comfortable.

Figures 11A, 11B:
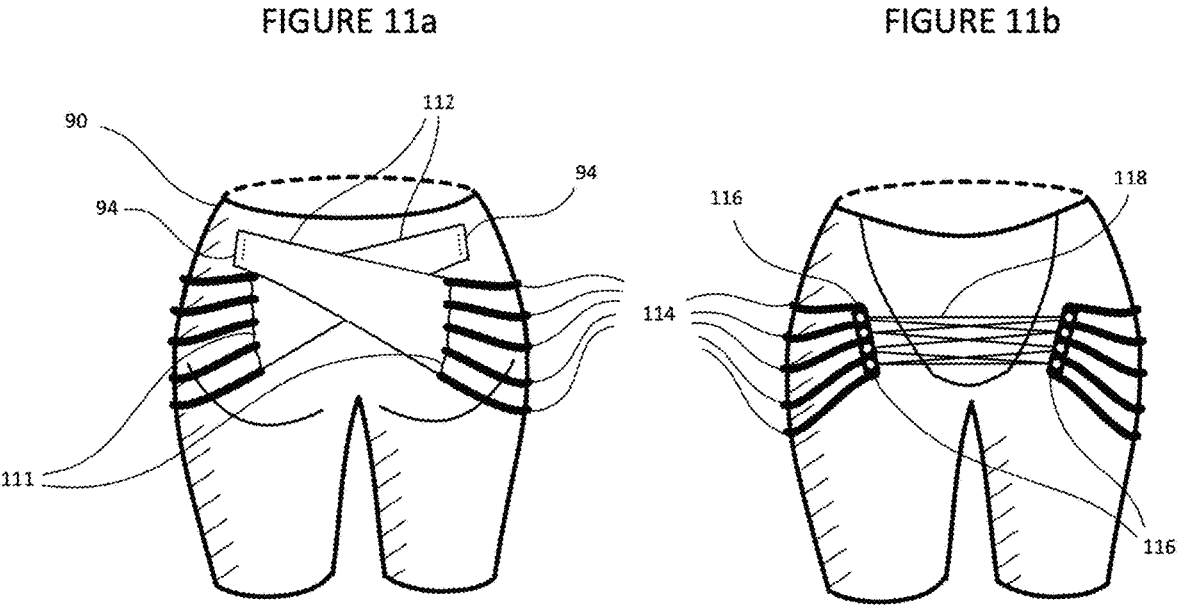
FIGS. 11a and 11b show an illustration of an embodiment of a hip orthosis suitable for controlling hip dislocation that uses conformable fingers to control the forces across the hip joint.

FIGS. 11a and 11b are illustrations of a hip orthotic suitable for applying a force to prevent hip dislocation. The wings (92) of FIGS. 9a, 9b, and 10 are replaced by a fabric (112) and flexible finger (114) combination. One distal end (94) of the fabric (112) is secured to a garment (90). The one distal end of the fingers (114) is secured to the other distal end of the fabric (111). The fingers wrap around the hip and can be contoured to match the shape of the wearer. The other distal end of the fingers is secured to a lacing element (116). In aspects, a crossed lace tensioning system (118) secures the two sets of fingers. Tightening the laces pulls the lace elements (116) together. The angle and positioning of the lacing elements (116) and the angle and positioning of the distal ends (94) result in a force vector (not shown) that pulls the femur into the hip bone socket. The flexible fingers can be made of nylon, polyolefins, plastic, composites and the like.

Embodiments described herein have demonstrated an orthosis with a single tensioning point for each wing. The direction of the force that holds the femur in the hip bone socket is the result of the angles and locations of the two distal ends of the wings: a first end where the wing is attached to the garment or waist portion, and a second end upon which the tensioning element acts. The magnitude of the force is determined by the amount of tension that the tensioning element provides. At times it may not be possible to use just a single tensioning element to obtain the desired force direction or magnitude. A wound or injury may prevent the optimal placement of one of the ends of the wing on the wearer's body. It may also be that the optimal location of one of the ends of the wing falls outside the physical boundaries of the garment (or waist portion). This is especially a problem when the desire is to make the orthosis as compact and discreet as possible.

Figure 12:
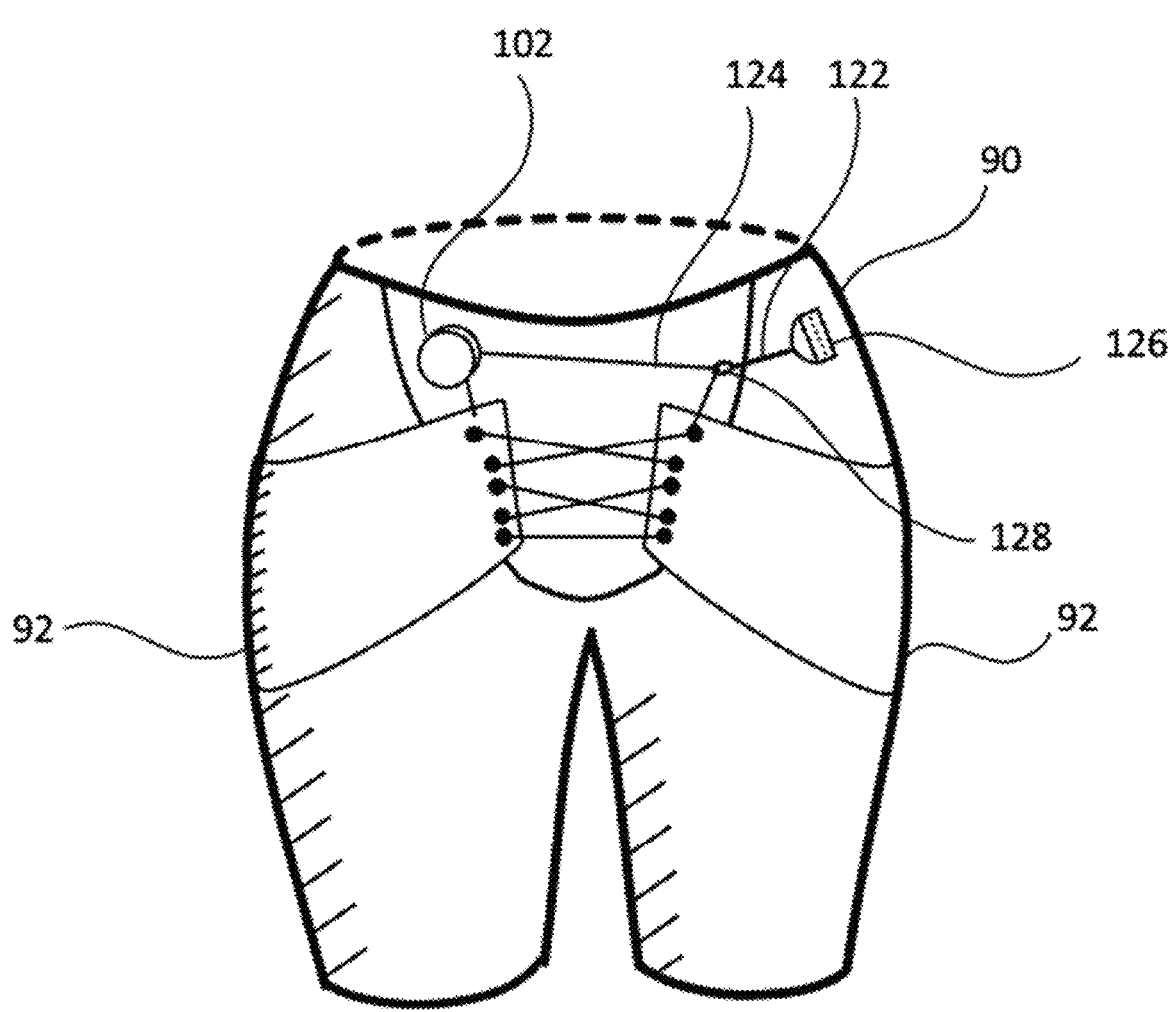
FIG. 12 shows an illustration of a hip orthosis with a passive, secondary tension element.

Additional tensioning points can be added to manipulate the desired force direction. For example, FIG. 12 shows an alternate embodiment of the hip joint dislocation orthotic shown in FIG. 10. A second tension element (122) has been connected to the cable (124) that is wound around the dial (102). The second tension element has one distal end (126) that is fixed to the garment (90). The second distal end (128) of the tension element (122) has an eyelet through which the cable (124) passes. As the dial is used to increase the tension on the wings, the force vector on the wing is a combination of the force vector created by the dial tension system and the force vector of the second tension element. This is an example of a passive second tension element. The amount of tension in the second tension element is dependent on the amount of tension applied by the dial tension system.

The form fitting brace secures the joint in a similar fashion as other embodiments described herein. When the elastic piece is anchored on the front of the thigh portion and is pulled under tension, it limits the backwards movement of the leg. When the elastic piece is anchored on the back of the thigh portion, the leg's ability to move forward is limited. The forces can be employed at the same time or separately. It is preferred that the forces have a vector that is primarily in the downward direction, limiting the movement upwards.

Figure 13:
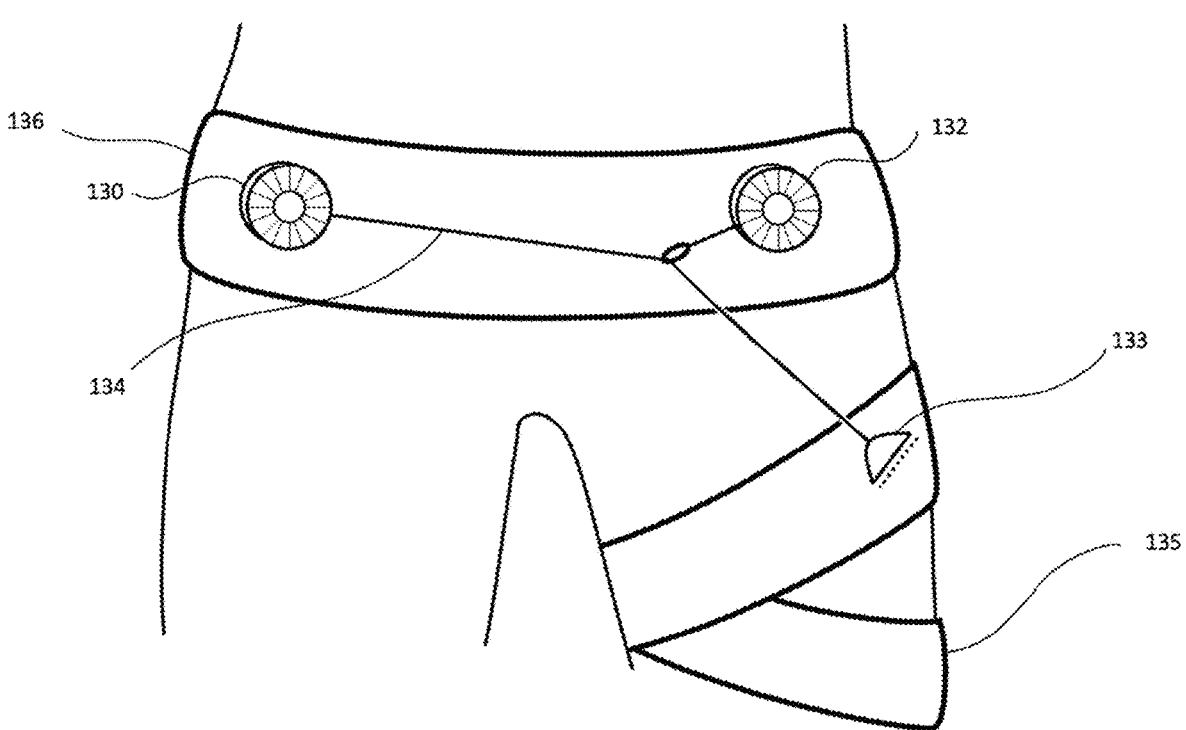
FIG. 13 shows an illustration of a hip orthosis with an active, secondary tension element.

FIG. 13 shows an orthotic with two independent tensioning systems. The orthotic has a waist portion (136) and a thigh portion (135). A first distal end of a cable (134) is attached to a dial (130), runs through a loop connected to a second tensioning dial (132), and is fixed at a second distal end (133) to the thigh portion (135). The first tensioning dial (130) predominantly controls the magnitude of force acting on the joint. The second tensioning dial (132) is primarily used to manipulate the direction of the force. This is an example of an active second tension element. It is envisioned to combine one or more active and passive tensioning elements to achieve the optimum force direction and magnitude in a single orthotic.

For a patient suffering from osteoarthritis where their cartilage has degraded in the hip joint, walking may cause a tremendous amount of pain. The weight of their torso is supported in part by the topside of the ball of the femur on the upper side of the hip socket. Bone on bone contact is painful and the sliding/grinding motion of the bones together as the patient walks makes the pain worse. Activities where a large force is placed on one leg (such as going up stairs) makes the problem worse.

Figure 14:
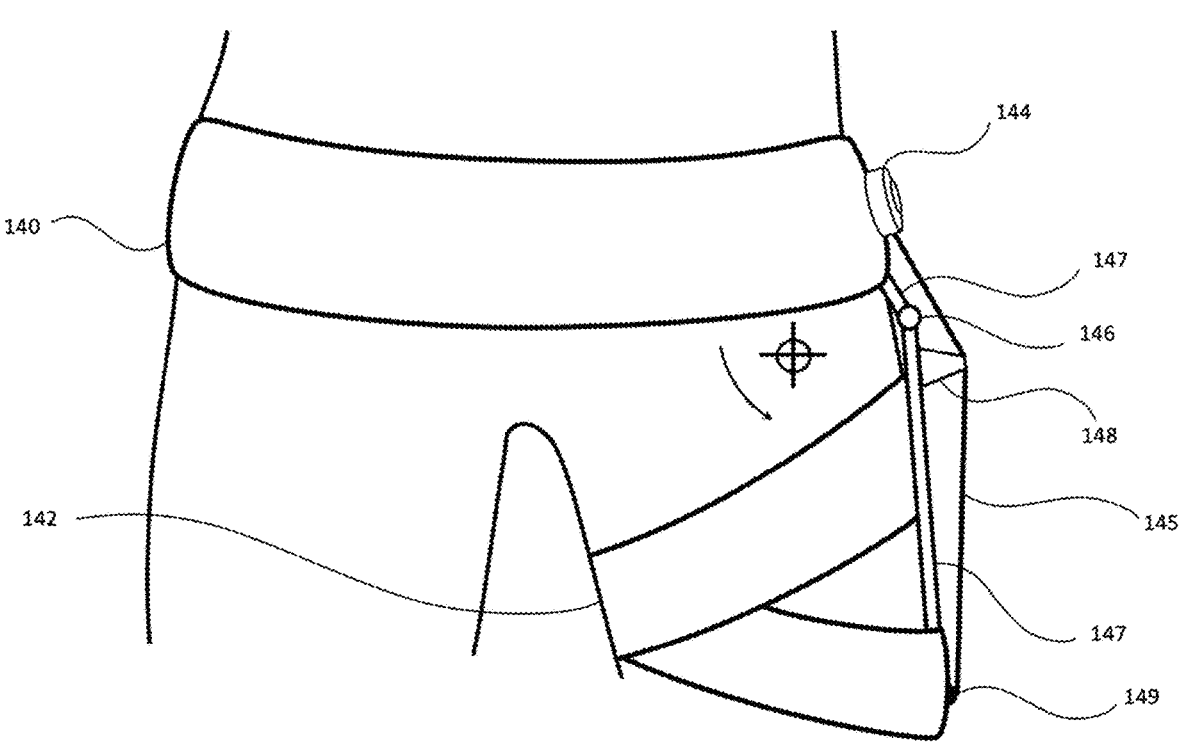
FIG. 14 shows an illustration of a distraction hip orthosis.

Pulling the femur into the hip bone (as traditional, currently-existing hip orthotics do) can, in aspects, make the problem worse. What is needed is a device to distract a ball and socket joint, like the hip joint. FIG. 14 shows a hip distraction orthotic according to the present invention. There is a waist portion (140) and a thigh portion (142). A first end of a flexible cable (145) is secured to an anchor point (149) on the thigh portion. A second end of a flexible cable is connected to a tensioning element (144) that is secured to the waist portion. For illustrative purposes, the tensioning element is shown a ratchet and pawl dial mechanism although other mechanisms such as a cam, lever, screw and nut, slide, rack and pinion, and the like, are envisioned. The cable can pass over a vector direction element (148) that is secured to the orthotic. The waist portion and thigh portion are connected by a stiff element (147) with a hinge (146). Turning the dial increases the tension on the cable. The tension on the anchor element on the thigh portion produces a moment of rotation on the wearer's leg about the hinge (146). This, in turn, creates a moment of rotation of the femur. The center of the femoral ball is shown schematically with the crosshairs in FIG. 14. The direction of rotation of the femoral ball is shown by the curved arrow. This creates a downward force on the femoral ball which distracts the hip joint in the desired direction and thus reduces the effective weight pressing the femoral ball into the hip socket creating relief for the wearer of the orthotic.

The invention shown in FIG. 14 can be considered a partial or directional distracting orthotic. The distraction occurs in a desired, beneficial direction only; the rest of the joint remains unaffected, in embodiments. The dial (144) allows the wearer to select the amount of joint distraction desired. As shown in FIG. 14, the hip orthosis is configured to wear while the wearer is engaged in daily activities. In another embodiment, the orthosis is configured to wear for extended periods of time (e.g., many days or overnight). The joint distraction forces, while they may provide immediate relief, are, in aspects, meant to separate the femur and hip bone so that cartilage may regrow.

When the optimum location of a single tensioning element is not feasible, multiple tensioning elements and/or multiple vector direction elements can be positioned on, in, or along the orthotic. The direction and magnitude of the distracting force will be the result of the vector addition of all the tensioning elements. The tensioning elements may be active, passive, or combinations thereof. Multiple tensioning elements may be used to spread out the forces felt by the wearer of the orthotic or to reposition the pressure points to avoid tender, injured, or sensitive body parts of the wearer.

Figure 15:
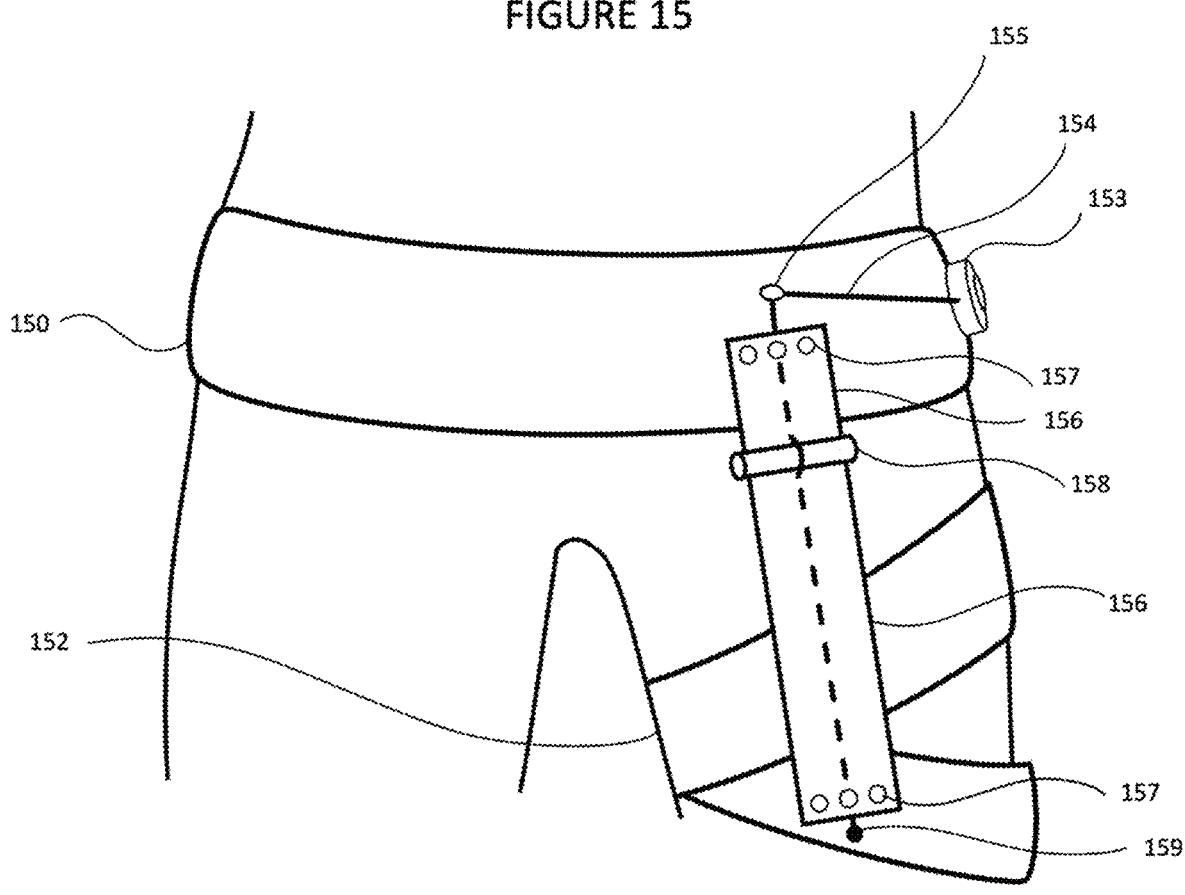
FIG. 15 shows an illustration of an unloading hip orthosis.

Elements of a distraction orthotic can be combined with elements of a traditional orthotic. For a patient suffering from osteoarthritis and hip dislocation, an ideal orthotic might distract in the coronal plane (up and down) but would hold and compress the femur to the hip around the transversal plane. Likewise, FIG. 15 shows an orthotic according to the present invention with a tensioning element or elements that can be used to partially unload the weight of the leg making it easier for the wearer to lift that leg. A waist portion (150) and a thigh portion (152) are connected by a hinge mechanism (156). The distal ends of the hinge (157) are attached to the waist and thigh portions, and a pivot (158) allows the leg to move in the sagittal plane. A tensioning element (153) is attached to the waist portion. A cable (154) runs from the tensioning element to a loop (155) also attached to the waist portion. The loop changes the direction of the tensile force applied by the tension element. The cable mostly runs underneath the hinge mechanism (shown in dotted lines) but exits the tunnel under the hinge mechanism to pass in front of the pivot (158). The distal end of the cable is attached on the thigh portion at the anchor point (159). By applying a tension via the tensioning mechanism, the resultant forces help lift the leg in the sagittal plane partially unloading the weight of the leg.

The single pivot point such as shown in FIG. 15 is positioned in front of the axis of rotation in the sagittal plane of the hip joint. When the leg swings forward, the pivot point moves backwards and may be uncomfortable for the wearer. By using a multitude of pivot points in the hinge (157), the hinge can flex and conform in the sagittal plane without pinching the wearer and can still provide motion control in the coronal plane.

According to embodiments of the present invention, a hip orthotic can be configured to unload the weight on a hip joint to relieve osteoarthritis, to limit range of motion or supplement weak muscle groups to provide stability, to compress the ball and socket joint to prevent dislocations, assist in gait control, or combinations thereof. These functions rely on manipulating a force (or forces) across the hip joint. In some applications, it is desirable to provide a counter-force while applying a force. For example, the hip dislocations most commonly occur when a straight leg is abducted. An orthotic that assists in abduction (for patients with gluteal abduction deficiency) could leave the patient more susceptible to hip dislocation. A compression band that wraps around the hip and provides a constant hoop-stress force may help but could be uncomfortable. It would be better, according to aspects of the present invention, to provide a counter-force that compresses the femoral ball into the hip socket at the time that the hip is abducted.

It is known that the acetabular side of the hip socket is a shallow and thus the anterior muscle groups must work harder to support the hip. If these muscle groups tire or if they become injured this can lead to hip joint instability. In such cases, off-loading the weight on the hip from the back would be desirable to allow the anterior muscle structures to relax and/or heal. Older patients with weakness or tears in the gluteus minimus often develop a contralateral pelvic drop which is currently treated with a cane or walker. For these patients, an unloading hip orthotic according to the present invention would increase their mobility.

Osteoarthrosis hip pain is difficult to treat surgically. Offloading weight from the hip joint and/or limiting range of motion are two non-surgical solutions that can be addressed by the presently described hip orthotic.

It is possible to use a hip orthotic to assist and/or control the gait of the patient. Range of motion stops according to the present invention lock out unwanted motion—for example, they can prevent hyperextension. FIG. 20*a* is an orthogonal view of another aspect of a hemispherical hinge (200) according to the present invention that has a range of motion stop particularly suitable for ball and socket joints. The cup of one arm (203) is sandwiched by the two cups of the second arm (202) as shown in the sectional view in FIG. 20*b*. A slot (205) is cut through both arms and a pin (204) is positioned in the slot. The arms can rotate without hindrance along the z axis (as shown in FIG. 19*a*) however they can only rotate about the y-axis until the pin hits the limits of the slot.

Figure 22:
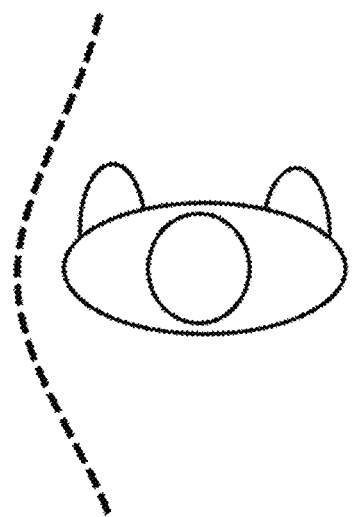
FIG. 22. is a top down view of the gait resulting from the hinge of FIG. 21.

In some cases, it is desirable to provide feedback to the patient so that they can learn what motions are appropriate when they are not wearing the hip orthotic. Configurating a tension element across the joint using a cammed or variable radius path can make some ranges of motion increasingly difficult for the patient instead of a hard stop. This type of tensioning system according to the present invention is particularly useful for gait adaptation and learning, because it allows the body to develop natural muscle memory. FIG. 21 is another aspect of a gait adaptation hip orthotic hinge (210) according to the present invention. A first arm (211) of the hinge is connected to a waist portion (not shown). A second arm (212) of the hinge is connected to a thigh portion (not shown). A connector element (213) joins the first and the second arms with two orthogonal axes of rotation. A tension element (215) is affixed to the first and second arms. The path of the tension element takes it over a variably height ramp (216). As configured in FIG. 21, when the leg of a patient wearing a hip orthotic with the hinge (210) is at 0 degrees flexion (that is, standing up straight), the tension element pulls the second arm (212) into hip abduction. When the leg is swung forward (or backwards), the force by tension element on the second arm is reduced allowing the leg to swing back to the neutral position. FIG. 22 is a top view of a schematic of a patient wearing a hip orthotic with the hinge of FIG. 21. The dashed line in FIG. 22 shows the position of the patient's leg as they flex or extend it.

It is preferable that the wearer of an orthotic can increase or decrease the amount of distraction based on their current activity, even completely removing the distracting forces entirely at times (e.g., when lying down). In embodiments of the present invention, the ratchet and pawl dial mechanism has a quick release button that completely releases the tension in the tensioning element. Other means of releasing the tension such as a two-position lever, an adjustable cam, a slider with a catch, etc., could all be used to disengage the tension of the distraction element.

The various embodiments described above can be combined with other therapeutic mechanisms such as electrodes for electrostimulation therapy, peristaltic compression cuffs for muscle massage and blood flow stimulation, pockets or attachments for ice pack or hot pack therapy, Peltier cooling devices for cooling therapy, heat pads or zones for heat therapy, and/or straps for blood flow restriction therapy.

The adjustable tensioning element in embodiments described herein can give the wearer the ability to customize the degree of security and immobilization they want with the brace. It is envisioned that the wearer can further customize the orthosis by, for example, replacing the elastic element with alternate elastic elements (or non-elastic materials) with different properties to fine tune the forces applied by the cabling system. This gives the wearer more ability to customize their fit and strength of the brace.

Another advantage of the invention is that braces can be donned by the wearer without tension applied, making it easy to put on or take off. Once the brace is put on by the wearer, the tension can be adjusted up or down. This can be varied for different activities in real time or substantially real time. This gives the wearer the ability to adjust the forces on the joint depending on how it feels when secured in the brace.

EXAMPLES

Multi-Axis Rotation Control Hip Brace with Proximal and Distal Portions connected by a Tensioning Element. The device contains an adjustable tensioning system. The tensioning element in this case represents one type of energy storage element, in this case under tension. The tensioning element in this example further comprises a tensioning element, a rigid cable and an adjustment mechanism. The adjustment mechanism, in aspects a rotary dial, is embedded in an adjustable mechanism insert within the thigh portion. It may be held in place by the form of a locking mechanism, where the dial's male end is complementary with the female insert in the thigh portion. It may be sewn or glued or otherwise bonded into the thigh portion. Regardless of the method, the adjustable mechanism insert can ensure that the adjustment mechanism is securely in place when subjected to any force subjected by the wearer intentionally or inadvertently by the wearer, including but not limited to rotation in either direction, or pulling out. The adjustment mechanism is, in aspects, further connected to the cable, for example by a knot. The term cable herein generally refers to any type of cable, wire, braid, string, chain, lace, rope, or article, that is flexible or substantially flexible yet substantially not extensible and is able to be wound up and transmit tensile forces, as would be understood by one of ordinary skill in the art.

The cable or cables may optionally be attached to the one or more tensioning element, which is inserted into another portion of the apparatus, and may be anchored in a slot within the other portion. When tension is applied to the tensioning element, the other portion is pulled towards the thigh portion. This would generate a torque around the top of the hip joint. It would also generate a force pulling the thigh portion into the hip, e.g. providing a compressive pressure within the hip joint. Anchoring the tensioning elements in other positions around the joint (e.g., anterior or posterior to the joint) would provide a different direction of force around the joint. Such force could supplement muscle, tendon or ligament function, or limit range of motion in a direction.

The adjustment mechanism can allow the wearer to change the magnitude of force within the tensioning element, and therefore the force around the joint based on their need. In some embodiments, the adjustment mechanism allows tension to be increased in one direction, e.g., by clockwise rotation of a dial. The tension may be released rapidly by disengaging the dial, e.g., by pulling it out, pushing it in, or pressing a button. In other embodiments, the adjustment mechanism may allow gradual increase or decrease of tension. For example, clockwise rotation of a rotary dial would increase tension, while counterclockwise rotation of the dial would reduce tension. The adjustment mechanism may be a rotary dial, a lever, a switch, a ratchet and pawl mechanism, a pulley, or an electronic adjustment mechanism operated by a motor (and/or a controller). The adjustment mechanism may be placed in an optimal position for use that is non-obstructive during activity, but accessible, for example at the rear of the thigh portion.

Multi-Axis Rotation Control Hip Brace with Proximal and Distal Portions connected by a Hinge. This embodiment is comprised of a proximal thigh portion and distal portion connected by one or more hinges and a tensioning system. The proximal thigh portion and distal portion are constrained to articulate in a specific axis, or axes based on the type or position of the hinge(s). However, the embodiment contains functionally equivalent descriptions of the components of the adjustable tensioning apparatus including the adjustment mechanism, the adjustable mechanism insert, one or more cable, and a tensioning element. The tensioning element in this case represents one type of energy storage element, in this case under tension.

The way the cable or cables are connected to the adjustment mechanism may change how forces are applied on one or more cables, e.g., adding tension to one while decreasing tension on another, or providing equivalent tension to both cables. In the same way, tension may be increased on one side of the cable and decreased on the other side of the cable.

The cables may be connected directly to the distal portion, therefore directly connecting the adjustment mechanism and the distal portion. The cables may also be indirectly attached to either the adjustment mechanism and/or the distal portion. Indirectly attached can mean, for example in this embodiment, being connected to described components, e.g. a cable may be indirectly attached to the distal portion by attaching to a tensioning element, wherein the tensioning element is directly attached to the distal portion. In aspects, these may be connected in line with one another. Such an example is shown in this embodiment, where the cable is indirectly connected from the adjustment mechanism to the distal portion by a tensioning element and anchors.

The anchors, as described herein, generally refer to any type of anchor, hook, hook and loop materials, button, screw, knot, guides, sliders, eyelets, fastener, insert or connecting mechanism, that exist between components of the tensioning apparatus, proximal portion, and/or distal portion. The location of the anchors on the tensioning element, proximal thigh portion, or distal portion, may be changed to control the direction of force around the joint. They may be set during fabrication or may be moved by the wearer or professional as necessary to change the direction of force.

The tensioning element can be connected to a distal portion. As such, the proximal thigh portion can be connected to the distal portion by the tensioning element, which runs across or near the leg joint. By example, the tensioning element may be connected to the distal portion with hooks, hook and loop materials, screws, knots, fasteners, inserts or anchors, or a melding of material with the tensioning element. The tensioning element and the distal unit may also be manufactured as one continuous piece, for example as a 3D printed or molded thermoplastic material.

The adjustment mechanism can allow the wearer to change the magnitude of force within the tensioning element, and therefore the force around the joint based on their need. In some embodiments, the adjustment mechanism allows tension to be increased in one direction, e.g., by clockwise rotation of a dial. The tension may be released rapidly by disengaging the dial, e.g., by pulling it out, pushing it in, or pressing a button. In other embodiments, the adjustment mechanism may allow gradual increase or decrease of tension. For example, clockwise rotation of a rotary dial would increase tension, while counterclockwise rotation of the dial would reduce tension. The adjustment mechanism may be a rotary dial, a lever, a switch, a ratchet and pawl mechanism, a pulley, or an electronic adjustment mechanism operated by a motor (and/or a controller). The adjustment mechanism may be placed in an optimal position for use that is non-obstructive during activity, but accessible, for example at the rear of the proximal thigh portion.

One or more channel in the proximal thigh portion can, in aspects, guide the positioning and orientation of the cables, therefore controlling the direction of force. The channel may be unique to the specific model of brace, or it may be custom to the individual based on the precise direction of support that they require.

By way of example, a proximal fabric (semi-rigid) thigh portion may anchor the device to the hip. The proximal thigh portion may also be connected to another body part or position above the hip joint. The proximal thigh portion may be rigid or semi rigid to fit to the user's upper leg. The distal portion will attach or conform to the user's thigh or provide additional support and to maximize comfort. The distal portion may be comprised of a rigid or semirigid custom or off the shelf hip brace or thigh portion brace. The distal portion may work synergistically with the adjustable tensioning mechanism to optimize the joint geometry, modify forces within other lower limb joints such as the wrist, elbow and leg, and modify thigh portion movement/range of motion.

The energy storage element, in this example a tensioning element, may comprise rigid, semi rigid, elastic or spring elements, individually or in combination. Force may be stored within the energy storage element to generate a torque or force around the desired axis or combination of axes of the joint. The modularity of the device enables this axis of rotation to be changed, either in manufacturing, by the clinician or by the wearer. For example, by positioning the tensioning element on the lower side of the leg, dislocation may be prevented. Alternatively, the tensioning element placed anterior to the leg may replace the function of the tendon. The direction of the net force vector and positioning of forces around the joint to control range of motion may be modified by positioning of the channels or guides within the proximal portion through which the cable or cables run. Additionally, direction of the net force vector and positioning of forces around the joint to control range of motion may be modified by the shape of the tensioning element, for example an elastomeric band with one point of connection between the proximal and distal portions vs. an elastomeric web with two points of connection to the distal portion vs. an elastomeric sheet continuously connected along the distal portion would change the distribution and direction of the net force vector.

Overall, the embodiment allows for customization to fit the wearer's specific need(s) in many aspects. The magnitude of force can be modified by the adjustment mechanism and by the material properties and geometry of the tensioning element. The direction of force and axis of rotation can be modified by the adjustment mechanism, the channel location on the proximal thigh portion, the location and number of anchor points between the cable and the tensioning element, the geometry of the tensioning element, and/or the location of the connection between the tensioning element and the distal portion. Through these mechanisms, rotation can be limited or controlled in one or more of the ML, AP and vertical axes to stabilize, correct, compress or unload the hip joint. The device can then therefore be engaged to restore proper leg orientation or joint geometry.

Methods of Use

The device in embodiments described herein are designed to maximize ease of use and comfort for the user. The device can be comprised of lightweight, durable materials including fabrics, plastics, elastomers, and 3D printed thermoplastics. In aspects, the wearer can rapidly (within 10-30 seconds, by way of example) don and doff the device. In some embodiments, the proximal thigh portion and distal portion may be flexible so that the wearer can stretch the material to slide their leg and hip into the device. In other embodiments, the device may contain an opening, for example made of hook and loop, so that the wearer can open and close the device to don and doff. The device can be manufactured to have a low profile, to fit comfortably and conveniently within the wearer's garments. Alternatively, the device may connect to the wearer's garments internally or externally.

In the various embodiments of the present disclosure, the magnitude and direction of force applied (or resistance or tension generated in the brace) can readily be tailored to the wearer based on their size, weight, joint geometry, injury, and desired activity. Braces as described herein can be light-weight, robust, low-profile, and well-fitting to users. Unlike braces in the prior art, those disclosed herein can be narrow and lightweight to be worn under clothing.

The various embodiments of the hip brace of the present disclosure can be used, by way of non-limiting examples: prophylactically to prevent injury; to reduce joint pain (e.g. during physical exercise or athletic competition); to rehabilitate existing injuries; postoperatively (e.g., high tension braces to immobilize the joint to a comfortable level within one or more desired range of motion); to assist or augment movement within a desired direction (e.g., in a direction limited by muscle, tendon or ligament deficiency or damage); and to provide stability and alignment to the joint.

The device described in embodiments can correct the position of the leg relative to the wearer's hip to restore proper range of motion or functionality. In other uses, the wearer may apply the device in embodiments to augment movement of the joint in one or more directions. For example, an athlete intending to increase leg-lifting force could use a device containing an elastomeric tensioning element on the proximal side of the hip. The wearer could 1) don the device, for example the device shown in the figures, 2) optionally adjust the position of the device, and 3) increase force in the tensioning element using the adjustment mechanism. Such an embodiment would reduce strain on the hips during walking and other activities.

In other uses, the wearer may apply the device in embodiments to support recovery or improve range of motion of the muscle, ligament, tendon, cartilage, and/or bone of the hip post-operation or post-injury. Additionally, the wearer may use the device to maintain joint function during the recovery period while protecting the joint from further damage. For example, for a wearer with a lateral tendon tear, the wearer would 1) don the device, for example shown in the figures, 2) optionally adjust the position of the device, and 3) increase force in the tensioning element using the adjustment mechanism to prevent inversion while allowing range of motion in other axes, therefore protecting the lateral ligaments from further strain.

The embodiments described can unload a region of the hip joint based on the direction and magnitude of force generated by the tensioning element. This can be achieved in one aspect by generating a counterforce on one side of the hip to reduce contact force on the opposite side. For example, by engaging an elastomeric tensioning element on the anterior side of the wearer's hip, the posterior side of the hip will be separated. This will separate the lateral side of the hip, and act as a spring to reduce the force within that region of the joint upon impact with the ground at each step. The mechanism can also reduce forces in an osteoarthritic or damaged region of the joint by altering the wearer's range of motion. The anterior region of the hip can be shielded from more significant forces that the wearer would normally experience without use of the device.

The device is designed such that it may be worn over or under the wearer's clothing. These embodiments may also be equipped with at least one sensor that collects useful information on rotation, range of motion, biomechanics, and health of the joint. This information may then be used to tailor or tune the device more precisely to the needs of the wearer or to inform a medical professional of information helpful in making decisions on a rehabilitation or treatment regimen, including decisions related to surgical procedures and joint implants. The device can also augment the function and performance of the joint post-operatively and complement the function of an implanted device or component, actively or passively.

In aspects, the hip brace comprises a portion for attaching to a leg of a wearer of the hip orthosis; a portion for attaching to a waist of the wearer of the hip orthosis; and at least one tensioning element, elastomeric band, elastomeric web, or elastomeric material, connected directly or indirectly to the portion for attaching to the leg and the portion for attaching to the waist, wherein the at least one tensioning element, elastomeric band, elastomeric web, or elastomeric material, exert a force or forces to influence one or more axes of rotation of a hip joint of the wearer; wherein the force or forces is variable with regards movement of the hip joint.

In aspects, the orthosis for a hip further comprises one or more slots, wherein the one or more slots are optionally contained within at least one side of one or more hinges of the orthosis.

In aspects, the orthosis for a hip described herein includes wherein the portion for attaching to the leg optionally connects to a leg orthosis, wherein the leg orthosis optionally connects to a knee or an ankle orthosis, and wherein the knee or ankle orthosis optionally connects to a foot orthosis.

In aspects, the dynamic hip orthosis comprises:
a portion for attaching to a leg of a wearer of the dynamic hip orthosis;
a portion for attaching to a waist of the wearer of the dynamic hip orthosis; and
at least one tensioning or compression apparatus comprising an adjustment mechanism and one or more cables directly or indirectly connecting the portion for attaching to the leg to the portion for attaching to the waist;
wherein the adjustment mechanism is capable of adjusting and/or controlling a force or forces across and/or around one or more axes of rotation of a hip joint of the wearer; and
wherein a magnitude of the force or forces, a direction of the force or forces, or both, are substantially constant in a first plane of motion, and the magnitude of the force or forces, the direction of the force or forces, or both, are variable in a second plane of motion, based on an increase or a decrease in a distance between the portion for attaching to the leg and the portion for attaching to the waist in response to movement of the leg of the wearer, the hip of the wearer, or both.

In aspects, this dynamic hip orthosis allows for the force or forces to be modified by the wearer while the wearer is wearing the dynamic hip orthosis.

In other aspects, the force or forces provided by the hip orthosis are capable of being toggled from a high state to a low state by the wearer while the wearer is wearing the dynamic hip orthosis.

In aspects, the hip orthosis comprises a portion for attaching to a leg of a wearer of the hip orthosis; a portion for attaching to the waist of the wearer of the hip orthosis; a force directing portion; at least one of a cam or a pulley; and a tensioning or compression apparatus comprising an adjustment mechanism and one or more cables directly or indirectly connecting the portion for attaching to the leg to the portion for attaching to the waist; wherein the adjustment mechanism is capable of adjusting and/or controlling a force or forces across and/or around one or more axes of movement of a hip joint of the wearer. In some aspects, the tensioning or compression apparatus runs over the at least one of a cam or a pulley to direct or amplify the force or forces in a direction chosen by the wearer.

In aspects, the present invention is a hip orthosis comprising:
a portion for attaching to a leg of a wearer of the hip orthosis;
a portion for attaching to a waist of the wearer of the hip orthosis; and
at least one tensioning element, elastomeric band, elastomeric web, or elastomeric material, connecting the portion for attaching to the leg and the portion for attaching to the waist, wherein the at least one tensioning element, elastomeric band, elastomeric web, or elastomeric material, exert a force or forces to influence one or more axes of rotation of a hip joint of the wearer;
wherein the force or forces is variable with movement of the hip joint; and
wherein a direction and a magnitude of the force or forces is tailorable to a need or needs of the wearer based on at least one of an injury type, a severity of an injury, and a morphology of the hip joint.

In aspects, the orthosis for a hip of a wearer can be partially or mostly integrated within a shirt, a jacket, a bodysuit, pants, or other clothing garment.

In aspects, the hip orthosis comprises a portion for attaching to a leg of a wearer of the hip orthosis; a portion for attaching to a waist of the wearer of the hip orthosis; and at least one tensioning element, elastomeric band, elastomeric web, or elastomeric material, connected directly or indirectly to the portion for attaching to the leg and the portion for attaching to the waist, wherein the at least one tensioning element, elastomeric band, elastomeric web, or elastomeric material, exert a force or forces to influence one or more axes of rotation of a hip joint of the wearer; wherein the force or forces is variable with movement of the hip joint.

In aspects, the current invention includes a distracting hip orthosis comprising: a leg portion; a waist portion; and a mechanism to push the leg portion and waist portion apart wherein the mechanism is capable of increasing the distance between the axis of rotation of the waist portion and the axis of rotation for the hip portion, as the waist portion and hip portions move with the body. In aspects, a direction of the force or forces results in a distraction force of a part of a femur from an acetabulum in at least one direction. In aspects, the orthosis can be capable of exerting, adjusting, and/or controlling a force or forces across and/or around one or more axes of rotation of a wearer's hip joint; wherein a direction of the force or forces results in a distraction of a part of a femur from an acetabulum in at least one direction.

It should be understood that the described embodiments are by example only. The same embodiments may incorporate springs or other energy storage elements to generate force across the joint in a similar fashion to the tensioning elements described. Additionally, adjustable compression mechanisms may substitute for the adjustable tensioning mechanisms to perform similar functions as described in the multi-axis rotation control brace.

In other embodiments, the hip orthosis may include magnets for fixation of parts, for generation of an electro-magnetic field that can be controlled by an actuator to generate forces around a joint, or to generally modify, limit, or control, joint geometry. In aspects, the magnetic system or electromagnetic field interacts with an implant within the joint or within the wearer's body, or with another component on the orthotic device. The joint implant and the orthosis may contain sensors that interact to drive function, adjustment of the tensioning systems, or generally provide data to the wearer or clinician for rehabilitative purposes.

In aspects, the invention includes a computer-implemented method of manufacturing a custom hip orthosis, the method comprising the following steps:

a. providing a three-dimensional ("3D") scan of a hip joint;

b. modeling a force or forces in the hip joint based on the 3D scan, user anatomical features, user-reported information, or combinations thereof;

c. designing a simulated digital hip orthosis with assistive and/or corrective forces as determined from the modeled force or forces; and d. fabricating the hip orthosis based on the simulated digital hip orthosis.

Embodiments of the invention also include a computer readable medium comprising one or more computer files comprising a set of computer-executable instructions for performing one or more of the calculations, steps, processes, and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EE-PROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer readable memory which may include random-access memory (RAM) or read-only memory (ROM). The computer-executable instructions can be embedded in computer hardware or stored in the computer-readable memory such that the computer or device may be directed to perform one or more of the calculations, steps, processes, and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks using text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection. In another embodiment, the user interface may be managed and controlled through an App or program on a phone, tablet, or other portable electronic device.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

One skilled in the art would recognize that similar adjustable tensioning and compression apparatuses could be applied to control rotation and forces around other joints including the wrist, shoulder, back, neck, knee, ankle, and elbow, by way of example.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all the references cited in this disclosure are each individually incorporated by reference herein in their entirety and as such are intended to provide an efficient way of supplementing the enabling disclosure of this invention as well as provide background detailing the level of ordinary skill in the art.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that while certain of the illustrations and FIG. may be close to the right scale, most of the illustrations and figures are not intended to be of the correct scale.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. An orthosis for a hip of a wearer comprising:
   a portion for attaching to a leg of the wearer;
   a portion for attaching to a waist of the wearer; and
   at least one tensioning or compression apparatus comprising at least one adjustment mechanism, at least one tensioning or compression element, and one or more cables directly or indirectly connecting the portion for attaching to the leg of the wearer to the portion for attaching to the waist of the wearer;
   wherein the at least one tensioning or compression element stores in-line tension or compression force or forces; and
   wherein the adjustment mechanism is operative to allow the wearer to adjust and/or control the in-line tension or compression force or forces across and/or around one or more axes of rotation of a hip joint of the wearer while the orthosis is being worn.

2. The orthosis for a hip of the wearer of claim 1, wherein the at least one tensioning or compression apparatus is operationally attached to or continuous with the portion for attaching to the leg, the portion for attaching to the waist, or both, or wherein the at least one tensioning or compression apparatus is provided between the portion for attaching to the leg and the portion for attaching to the waist.

3. The orthosis for a hip of the wearer of claim 1, wherein the at least one tensioning or compression element is or comprises one or more of: one or more elastomeric material, one or more band, one or more web, one or more webbing, one or more spring, one or more piston, one or more electromagnetic material, one or more energy storage element, or combinations thereof.

4. The orthosis for a hip of the wearer of claim 1, wherein the at least one tensioning or compression element is or comprises at least one elastomeric band, elastomeric web, or elastomeric material, capable of adjusting a force or forces along one or more axes.

5. The orthosis for a hip of the wearer of claim 1, further comprising one or more moveable anchor or anchor points, wherein the one or more moveable anchor or anchor points direct a force or forces generated by the at least one tensioning or compression apparatus across and/or around one or more axes of rotation of the hip joint of the wearer.

6. The orthosis for a hip of the wearer of claim 1, further comprising one or more hollow channels in or on the orthosis, wherein the one or more hollow channels contain one or more of the one or more cables, wherein the one or more of the one or more cables direct a force or forces generated by the at least one tensioning or compression apparatus across and/or around one or more axes of rotation of the hip joint of the wearer.

7. The orthosis for a hip of the wearer of claim 1, wherein the portion for attaching to the leg and the portion for attaching to the waist are connected by one or more hinges.

8. The orthosis for a hip of a wearer of claim 7, wherein at least a portion of a path of the one or more cables around the one or more hinges has a variable radius.

9. The orthosis for a hip of the wearer of claim 1, wherein the portion for attaching to the waist connects to and/or integrates with a back orthosis, a spine orthosis, or a hip orthosis, on an opposite side of a wearer's body.

10. The orthosis for a hip of the wearer of claim 1, wherein the adjustment mechanism is motorized, and wherein the in-line tension or compression force or forces stored by the at least one tensioning or compression element are adjusted or changed automatically, partially automatically, or manually, by the adjustment mechanism.

11. The orthosis for a hip of the wearer of claim 1, further comprising one or more sensors, wherein the one or more sensors collect information on wearer compliance, range of motion, biomechanical alignment and function, stability, relative position, movement patterns, joint health, biometrics, or combinations thereof.

12. The orthosis for a hip of the wearer of claim 11, wherein the information is used to design or modify the orthosis, to effect a function of other external or implantable devices, or to apply or adjust corrective or assistive force or forces across and/or around the hip joint of the wearer.

13. The orthosis for a hip of the wearer of claim 1, wherein the orthosis is configured to be affixed to the leg of the wearer and/or the hip of the wearer using a rigid material, a semi-rigid material, an inelastic material, an elastic material, or combinations thereof, wrapped around the hip of the wearer from a first part of the hip of the wearer and configured to be attached at a second part of the hip of the wearer.

14. The orthosis for a hip of the wearer of claim 1, wherein the at least one tensioning or compression element is or comprises one or more adjustable springs or one or more elastomeric element, wherein the one or more adjustable springs or the one or more elastomeric element store the in-line tension or compression force or forces.

15. The orthosis for a hip of the wearer of claim 1, wherein rigid, semi-rigid, or flexible materials or plates, support or interact with one or more of a chest, a back, the leg, or the hip of the wearer to stabilize either or both of the portion for attaching to the leg and the portion for attaching to the waist.

16. The orthosis for a hip of the wearer of claim 15, wherein the rigid, semi-rigid, or flexible materials or plates, are designed to fit the wearer based on body part and/or body joint measurements from a three-dimensional scan.

17. The orthosis for a hip of the wearer of claim 15, wherein the rigid, semi-rigid, or flexible materials or plates, include channels or pathways that are capable of being modified to direct or redirect a force or forces between the portion for attaching to the leg and the portion for attaching to the waist.

18. The orthosis for a hip of the wearer of claim 1, further comprising one or more sensors, wherein a force or forces generated by the at least one tensioning or compression apparatus are automatically adjusted based on information and/or feedback provided by the one or more sensors.

19. The orthosis for a hip of the wearer of claim 1, further comprising one or more moveable anchor points running along a locking track system, the locking track system running anterior to posterior along one or more axes of rotation of the hip joint of the wearer.

20. The orthosis for a hip of the wearer of claim 1, wherein one or more positions of the leg portion, the waist portion, or both, are capable of being fixed in a multitude of positions relative to one another, and wherein a range of motion of the leg portion relative to the waist portion is capable of being limited in either or both extension and flexion.

21. A hip orthosis comprising:
a portion for attaching to a leg of a wearer of the hip orthosis;
a sleeve for attaching to a waist of the wearer of the hip orthosis; and
at least one tensioning or compression element (a) directly or indirectly connected to an adjustment mechanism and (b) directly or indirectly connected to one or more cables, which directly or indirectly connect the portion for attaching to the leg to the sleeve for attaching to the waist;
wherein the at least one tensioning or compression element stores in-line tension or compression force or forces across and/or around one or more axes of rotation of a hip joint of the wearer; and
wherein the adjustment mechanism is operative to allow the wearer of the hip orthosis to adjust and/or control the in-line tension or compression force or forces across and/or around the one or more axes of rotation of the hip joint of the wearer while the orthosis is being worn by the wearer.

22. The hip orthosis of claim 21, wherein the one or more cables are removably attached to one or more different areas of the sleeve for attaching to the waist and/or the portion for attaching to the leg.

23. The hip orthosis of claim 21, wherein the one or more cables are connected to one or more cable guides.

24. The hip orthosis of claim 21, wherein the at least one tensioning or compression element is attached to or continuous with the portion for attaching to the leg, the sleeve for attaching to the waist, or both, or wherein the at least one tensioning or compression element is provided between the portion for attaching to the leg and the sleeve for attaching to the waist.

25. The hip orthosis of claim 21, wherein the at least one tensioning or compression element is or comprises an energy storage element, elastomeric material, elastomer, band, web, webbing, spring, piston, electromagnetic material, or combinations thereof.

26. The hip orthosis of claim 21, wherein the at least one tensioning or compression element is operably attached to one or more preset or predetermined locations on the portion for attaching to the leg, the sleeve for attaching to the waist, or both.

27. A hip orthosis system comprising:
a leg portion;
a waist portion;
one or more cables between the leg portion and the waist portion configured to connect the leg portion and the waist portion; and
an adjusting mechanism capable of holding, increasing, decreasing, maintaining, and/or releasing an in-line tension force or forces on the one or more cables;
wherein applying the in-line tension force or forces on the one or more cables generates a rotational force or forces around at least two of an anterior-posterior axis, a lateral-body axis, or a medial-lateral axis; and
wherein a location of one or more anchor points on the waist portion, the leg portion, or both, for the one or more cables, determines a direction or directions of the in-line tension force or forces.

28. The hip orthosis system of claim 27, further comprising one or more elastomeric element provided between the leg portion and the waist portion, and attached to the one or more connectors.

29. The hip orthosis of claim 27, further comprising a tensioning or compression element running over or through the one or more anchor points to direct or amplify a tensioning or compression force or forces in a direction chosen by the wearer.

*    *    *    *    *